(12) United States Patent
Slominski et al.

(10) Patent No.: US 7,253,293 B2
(45) Date of Patent: Aug. 7, 2007

(54) ENZYMATIC METHOD TO PRODUCE 7-DEHYDROPREGNENOLONE, VITAMIN D3-LIKE COMPOUNDS AND DERIVATIVES THEREOF

(76) Inventors: Andrzej Slominski, 930 Madison Ave., Suite 599, Memphis, TN (US) 38163; Robert Tuckey, 35 Stirling Highway, Crawley, WA 6009 (AU); Jordan Zjawiony, 132 Peyton Cir., Oxford, MS (US) 38655; D. Jeremy Stewart, 702 Markette St., Water Valley, MS (US) 38955; Jacobo Wortsman, 3128 Temple Dr., Springfield, IL (US) 62704

( * ) Notice: Subject to any disclaimer, the term of this patent is extended or adjusted under 35 U.S.C. 154(b) by 0 days.

(21) Appl. No.: 11/031,844

(22) Filed: Jan. 6, 2005

(65) Prior Publication Data

US 2005/0277171 A1 Dec. 15, 2005

Related U.S. Application Data

(60) Provisional application No. 60/534,602, filed on Jan. 6, 2004.

(51) Int. Cl.
*C07C 401/00* (2006.01)
(52) U.S. Cl. .................................................... 552/653
(58) Field of Classification Search ................ 552/606, 552/653
See application file for complete search history.

(56) References Cited

U.S. PATENT DOCUMENTS

| | | | |
|---|---|---|---|
| 3,786,062 A * | 1/1974 | Schroeder et al. ..........| 552/653 |
| 4,539,153 A * | 9/1985 | Vandewalle et al. ........| 544/229 |
| 6,372,926 B2 * | 4/2002 | Hesse et al. .................| 552/653 |
| 6,531,459 B1 * | 3/2003 | Steinmeyer et al. ........| 514/167 |
| 6,900,191 B1 * | 5/2005 | Moriarty et al. ............| 514/167 |
| 7,074,777 B2 * | 7/2006 | Kawase et al. .............| 514/167 |
| 2004/0259151 A1 * | 12/2004 | Jose et al. | |

FOREIGN PATENT DOCUMENTS

EP     0184112     * 6/1986

OTHER PUBLICATIONS

Shackleton et al., "Neonatal urinary steroids in Smith-Lemli-Optiz syndrome associated with 7-dehydrocholesterol reductase deficiency", Steroids, vol. 64, pp. 481-490, 1999.*
Holick et al., "Relationship of 25-hydroxyvitamin D3 side chain structure to biological activity", J. Biol. Chem., vol. 250(1), pp. 226-230, 1975.*
Guryev et al., "A pathway for the metabolism of vitamin D3: Unique hydroxylated metabolites formed during catalysis with cytochrome P450scc (CYP11A1)", Proc. Natl. Acad. Sci., USA, vol. 100(25), pp. 14754-14759, 2003.*
Woods et al., "Expression of catalytically active human cytochrome P450scc in *Escherichia coli* and Mutagenesis of isoleucine-462", Arch. Biochem. Biophys., fol 353(1), pp. 109-115, 1998.*

* cited by examiner

*Primary Examiner*—Barbara P. Badio
(74) *Attorney, Agent, or Firm*—Benjamin Aaron Adler

(57) ABSTRACT

Provided herein are enzymatic methods of producing steroid compounds such as 7-dehydropregnenolone, hydroxy derivatives thereof and vitamin D2- and D3-like compounds and derivatives thereof. Also provided are the derivatives of the vitamin D3-like compounds so generated via the action of cytochrome P450scc enzyme on substrates 7-dehydrocholesterol, vitamin D2 or vitamin D3.

1 Claim, 17 Drawing Sheets

Human

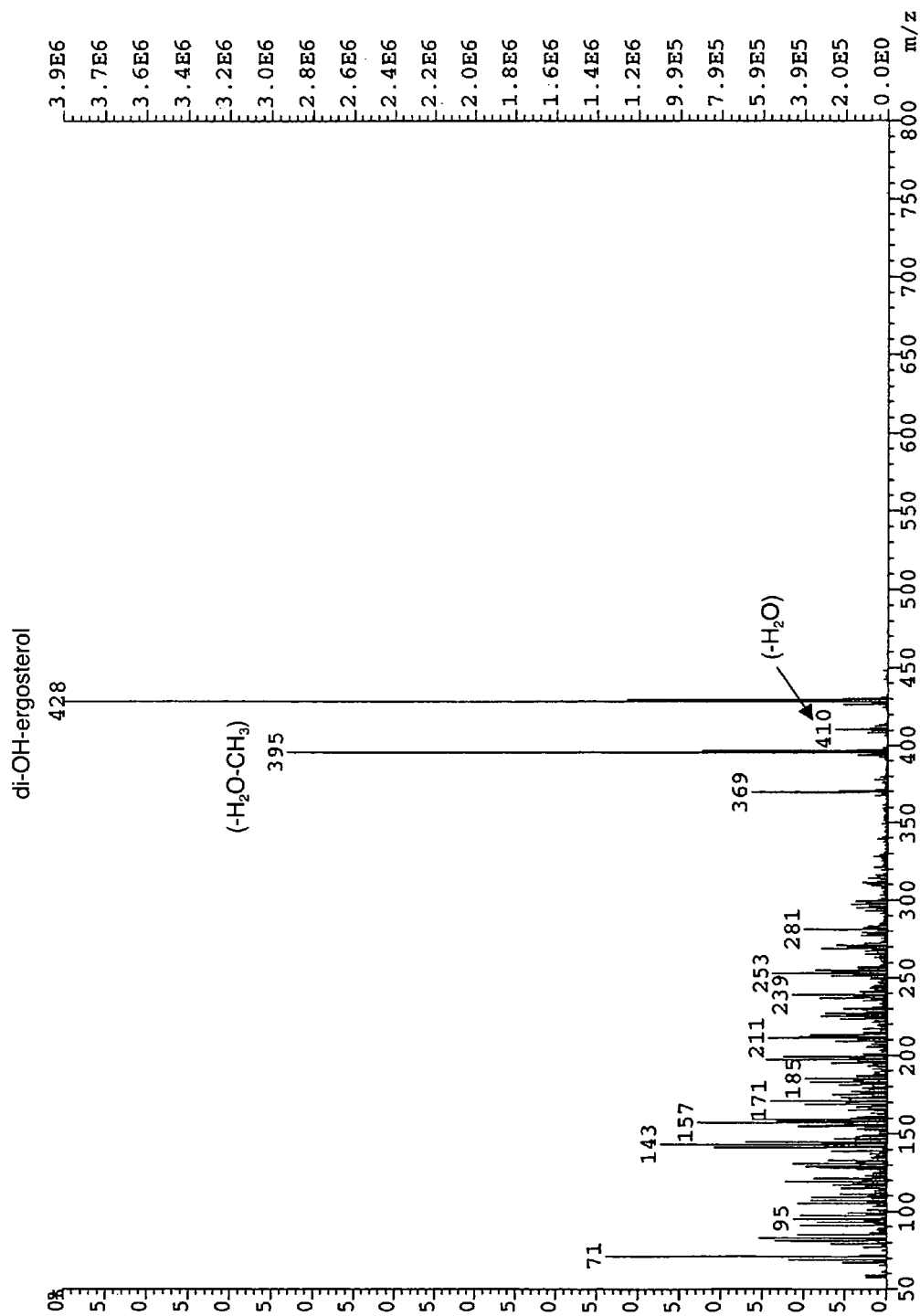

ENZYMATIC METHOD TO PRODUCE 7-DEHYDROPREGNENOLONE, VITAMIN D3-LIKE COMPOUNDS AND DERIVATIVES THEREOF

CROSS-REFERENCE TO RELATED APPLICATIONS

This non-provisional applications claims benefit of provisional U.S. Ser. No. 60/534,602, filed Jan. 6, 2004, now abandoned.

FEDERAL FUNDING LEGEND

This invention was produced in part using funds obtained through grant 1R01-AR047079-01A2 from the National Institutes of Health. Consequently, the federal government has certain rights in this invention.

BACKGROUND OF THE INVENTION

1. Field of the Invention

The present invention relates generally to the fields of enzymology and steroid chemistry. More specifically, the present invention relates to an enzymatic method of producing 7-dehydropregnenolone, vitamin D3-like compounds and derivatives thereof.

2. Description of the Related Art

The skin, the largest body organ, maintains internal homeostasis by not only separating the external environment from the internal milieu, but, also, through its immune and neuroendocrine activities (1-3). Cutaneous elements can, in addition, have powerful systemic actions, as is the case for vitamins D3 (1), which regulate calcium metabolism and modulate immune and neuroendocrine activities and proliferation and differentiation in cells of different lineage (4-6). Vitamin D3 is formed from the precursor steroid 7-dehydrocholesterol (7-DHC) localized mostly on the plasma membrane of basal epidermal keratinocytes which has 80% of skin 7-dehydrocholesterol content. Upon stimulation with photons of ultraviolet light B, i.e, light having a wavelength of 290-320 nm, 7-dehydrocholesterol undergoes photolysis to generate previtamin D3, which at normal skin temperature undergoes internal rearrangement to convert into vitamin D3 (4,7).

Cytochrome P450scc is a product of the CYP11A1 locus, thought until recently to use solely cholesterol as substrate, to hydroxylate and cleave the side chain at a single active site on the cytochrome to produce pregnenolone (8). Electrons for the hydroxylations are provided by NADPH through the electron transfer proteins adrenodoxin reductase and adrenodoxin (8-9) and cholesterol via transport StAR protein or MLN64 (20-21). The cholesterol substrate for P450scc is transported into mitochondria by specific cholesterol transporting proteins, StAR in testis, adrenal and ovary, and likely MLN64 in the placenta (20-21,23). Cholesterol transport by MLN64 in mitochondria may require proteolytic processing to release the 27-kDa cholesterol-binding domain from the full-length form associated with late endosomes (21,23). There also is evidence that the full-length 55-kDa form of MLN64 is associated with placental mitochondria (24). This biochemical pathway may be operative in the skin, since it expresses the related CYP11A1, CYP17, CYP21A2 and MC2-R genes (10).

Furthermore, skin and skin cells can rapidly and selectively metabolize progesterone and deoxycorticosterone (DOC) to a number of intermediates that include deoxycorticosterone, 18-hydroxydeoxycorticosterone and corticosterone, consistent with active local steroidogenesis (11-14). Recent information indicates an active P450scc system present in immortalized sebocytes. Cultured sebocytes converted 22R-hydroxycholesterol to 17-hydroxypregnenolone (22). Additionally, P450scc was detected by immunocytochemistry in human epidermis and hair follicle (22).

Interest in the P450scc system has been renewed by recent findings in patients with the rare Smith-Lemli-Opitz syndrome (SLOS) whose cholesterol synthesis from 7-dehydrocholesterol is impaired from deficiency of the 7-DHC-delta-7 reductase (15,16). Patients with Smith-Lemli-Opitz syndrome have noticeable amounts of 7-dehydropregnenolone (7-DHP) and its metabolites suggesting enzymatic production from 7-dehydrocholesterol (17,18). Furthermore, in most recent studies with an in vitro system of reconstituted P450scc, 7-dehydrocholesterol and vitamin D3 were found to serve as alternate substrates for cytochrome P450scc (19).

Epidermal availability of 7-dehydrocholesterol in conjunction with the presence of an active P450scc system makes it likely that 7-dehydropregnenolone is produced in the skin, albeit at low basal rates. Since the unsaturated B ring of 7-dehydropregnenolone is prone to breakage of the 9,10 carbon bond by UVB, and to further temperature dependent conversion, 7-dehydropregnenolone is probably transformed into the vitamin D3-like compound 5Z,7E-3β-hydroxy-9,10-secopregna-5,7,10(19)trien-20-one or vitDL (27). This conversion may be the explanation for the lack of elevation of vitamin D3 levels in spite of 7-dehydrocholesterol tissue accumulation in Smith-Lemli-Opitz syndrome patients (30). In fact, the skin, exposed to solar radiation, would be the site of choice for production of vitDL. Interestingly, native vitDL and its derivatives are known to possess immunomodulatory and anti-tumor properties (27).

The inventors have recognized that skin presents the unique situation of having readily available all the potential substrates for P450scc, e.g., cholesterol, 7-dehydrocholesterol and vitamins D2 and D3. This provides the background for the systematic investigation of cutaneous expression for each of the components of the P450scc enzymatic system. Furthermore, this also provides a basis to develop and test in vitro enzyme systems that use these substrates to produce new and useful steroids.

The prior art is deficient in the lack of an efficient and potentially large-scale enzymatic production of 7-dehydropregnenolone, vitamin D2-like- and vitamin D3-like compounds and derivatives thereof. Specifically, the prior art is deficient in the lack of a cytochrome P450scc enzyme system using 7-dehydrocholesterol, vitamin D3 or vitamin D2 as substrates to produce these compounds. The present invention fulfills this long-standing need and desire in the art.

SUMMARY OF THE INVENTION

The present invention is directed to a method of producing 7-dehydropregnenolone by enzymatically shortening a C17 side chain of 7-dehydrocholesterol via a cytochrome P450scc enzyme system to produce the 7-dehydropregnenolone. The method is directed further to thermophotolytically converting 7-dehydropregnenolone to a vitamin D3-like compound. The method also is directed further to enzymatically hydroxylating 7-dehydropregnenolone in at least one position to form at least one 7-dehydropregnenolone hydroxy derivative and thermophotolytically converting the 7-dehydropregnenolone hydroxy derivative(s) to at least one derivative of a vitamin D3-like compound. The method is directed further still to enzymatically converting 7-dehydroprognenolone to an androstadiene-like compound via P450c17 and thermophotolytically converting the androstadiene to a vitamin D3-like compound.

The present invention also is directed to a method of producing a vitamin D3-like compound by enzymatically hydroxylating a C17 side chain of ergosterol, vitamin D2, vitamin D3 or a combination thereof and enzymatically shortening the hydroxylated C17 side chain via a cytochrome P450scc enzyme system. Optionally, the hydroxylated ergosterol may be thermophotolytically converted to the hydroxylated vitamin D2 via UVB radiation and thermal intramolecular rearrangement at C9-C10. Alternatively, the C17 shortened ergosterol may be thermophotolytically converted at C9-C10 to form the vitamin D3-like compound. This method is directed further to producing hydroxy derivatives of the vitamin D3-like compound by enzymatically hydroxylating the vitamin D3-like compound at C11, C17, C20, or C21 or a combination thereof.

The present invention is directed further still to derivatives of ergosterol or vitamin D2 produced by the cytochrome P450scc enzyme system that are hydroxylated at least at position C20 within the C17 side chain. The present invention is directed further still to compounds comprising derivatives of vitamin D3-like or vitamin D2-like compounds derivatized at C11, C17, C20 or C21 or a combination thereof with hydroxy moieties or derivatized at C3, C17 or both with a carbonyl moiety.

Other and further aspects, features, benefits, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention are briefly summarized. The above may be better understood by reference to certain embodiments thereof which are illustrated in the appended drawings. These drawings form a part of the specification. It is to be noted; however, that the appended drawings illustrate preferred embodiments of the invention and therefore are not to be considered limiting in their scope.

Figure 1A:
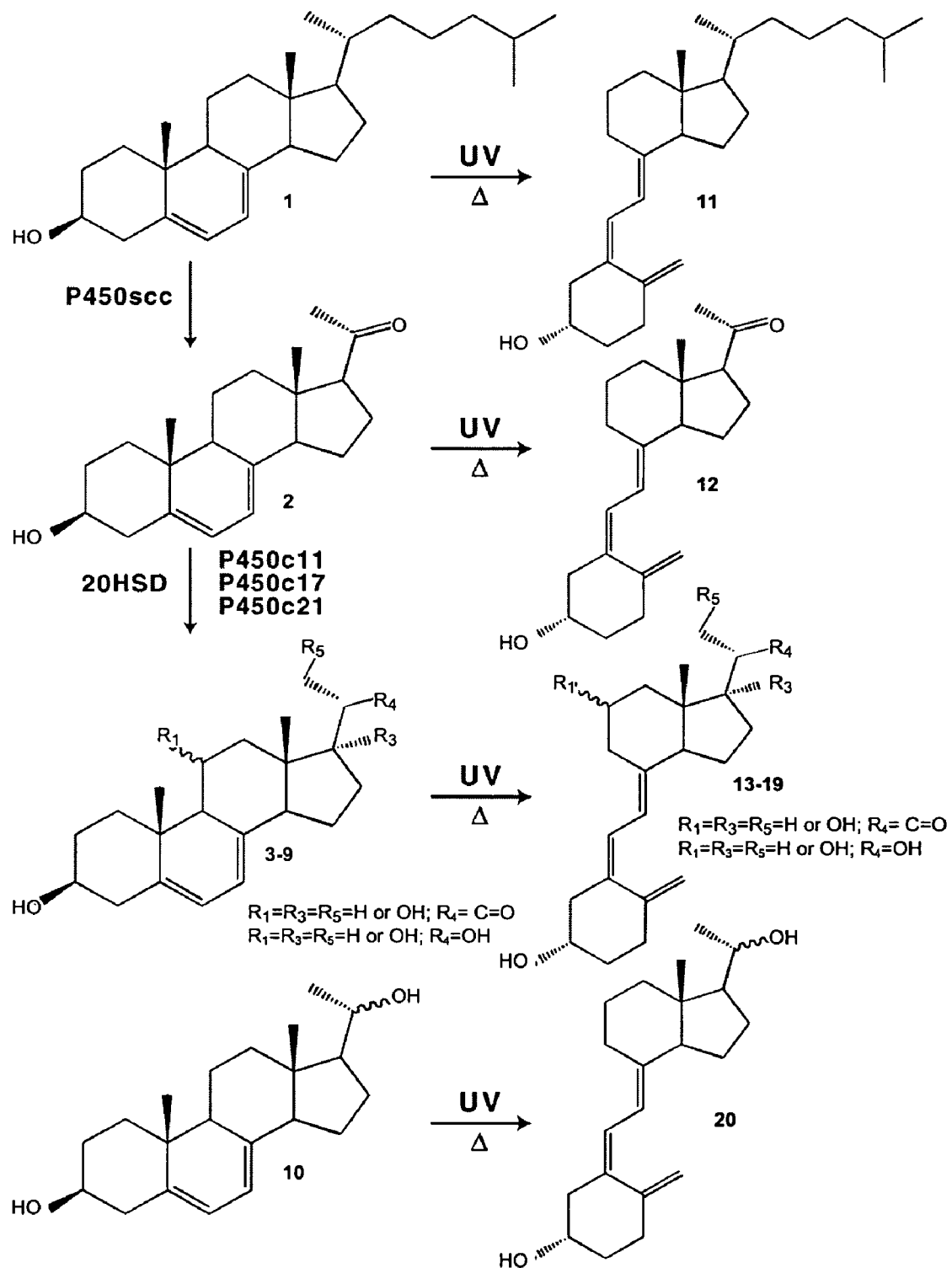
FIG. 1A depicts the metabolic pathway of 7-dehydropregnenolone production and its sequential transformation to vitamin D3 and the following hydroxy derivatives (#3-10) and/or to secosteroids (#12-20) generated by the action of UVB radiation.

1. cholesta-5,7-dien-3β-ol (7-dehydrocholesterol)
2. 3β-hydroxypregna-5,7-dien-20-one(7-dehydro pregnenolone)
3. 3β,11α or β-dihydroxypregna-5,7-dien-20-one
4. 3β,17β-dihydroxypregna-5,7-dien-20-one
5. 3β,21-dihydroxypregna-5,7-dien-20-one
6. 3β,17β,21-trihydroxypregna-5,7-dien-20-one
7. 3β,11α or β,17β-trihydroxypregna-5,7-dien-20-one
8. 3β,11α or β,21-trihydroxypregna-5,7-dien-20-one
9. 3β,11α or β,17,β,21-tetrahydroxypregna-5,7-dien-20-one
10. 3β,20α or β-dihydroxypregna-5,7-diene
11. 5Z,7E-9,10-secocholesta-5,7,10(19)-trien-3 1-ol (vitamin D₃)
12. 5Z,7E-3β-hydroxy-9,10-secopregna-5,7,10(19)trien-20-one
13. 5Z,7E-3β,11α- or β-dihydroxy-9,10-secopregna-5,7,10(19)trien-20-one
14. 5Z,7E-3,17β-dihydroxy-9,10-secopregna-5,7,10(19) trien-20-one
15. 5Z,7E-3β,21-dihydroxy-9,10-secopregna-5,7,10(19) trien-20-one
16. 5Z,7E-3β,17β,21-trihydroxy-9,10-secopregna-5,7,10 (19)trien-20-one
17. 5Z,7E-3β,11α or β,17β-tetrahydroxy-9,10-secopregna-5,7,10(19) trien-20-on
18. 5Z,7E-3β,11α or β,21-tetrahydroxy-9,10-secopregna-5,7,10(19) trien-20-one
19. 5Z,7E-3β,11α or β,17β,21-tetrahydroxy-9,10-secopregna-5,7,10(19)trien-20-one
20. 5Z,7E-3β,20α or β-dihydroxy-9,10-secopregna-5,7,10 (19)triene.

Figure 1B:
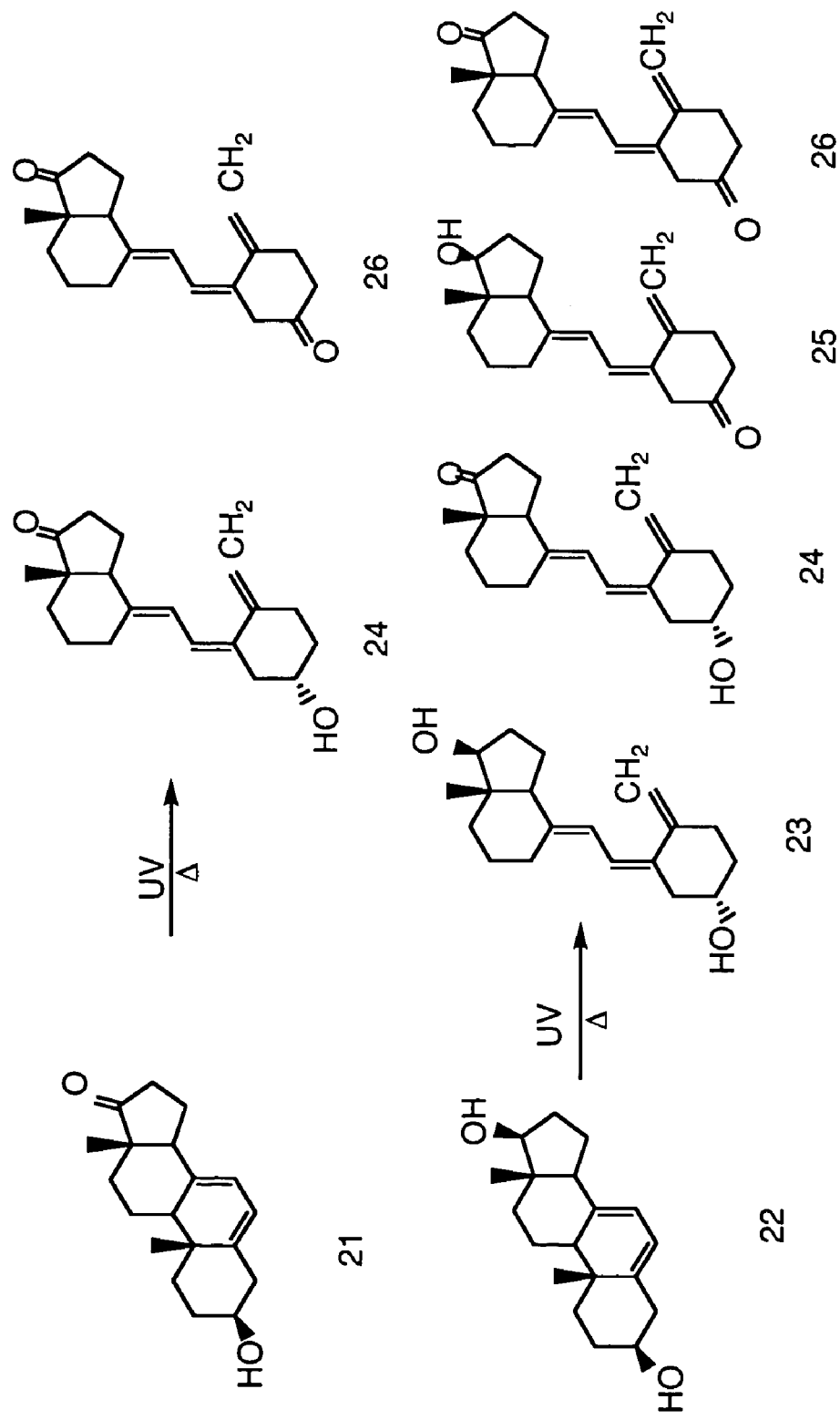
Figure 1C:
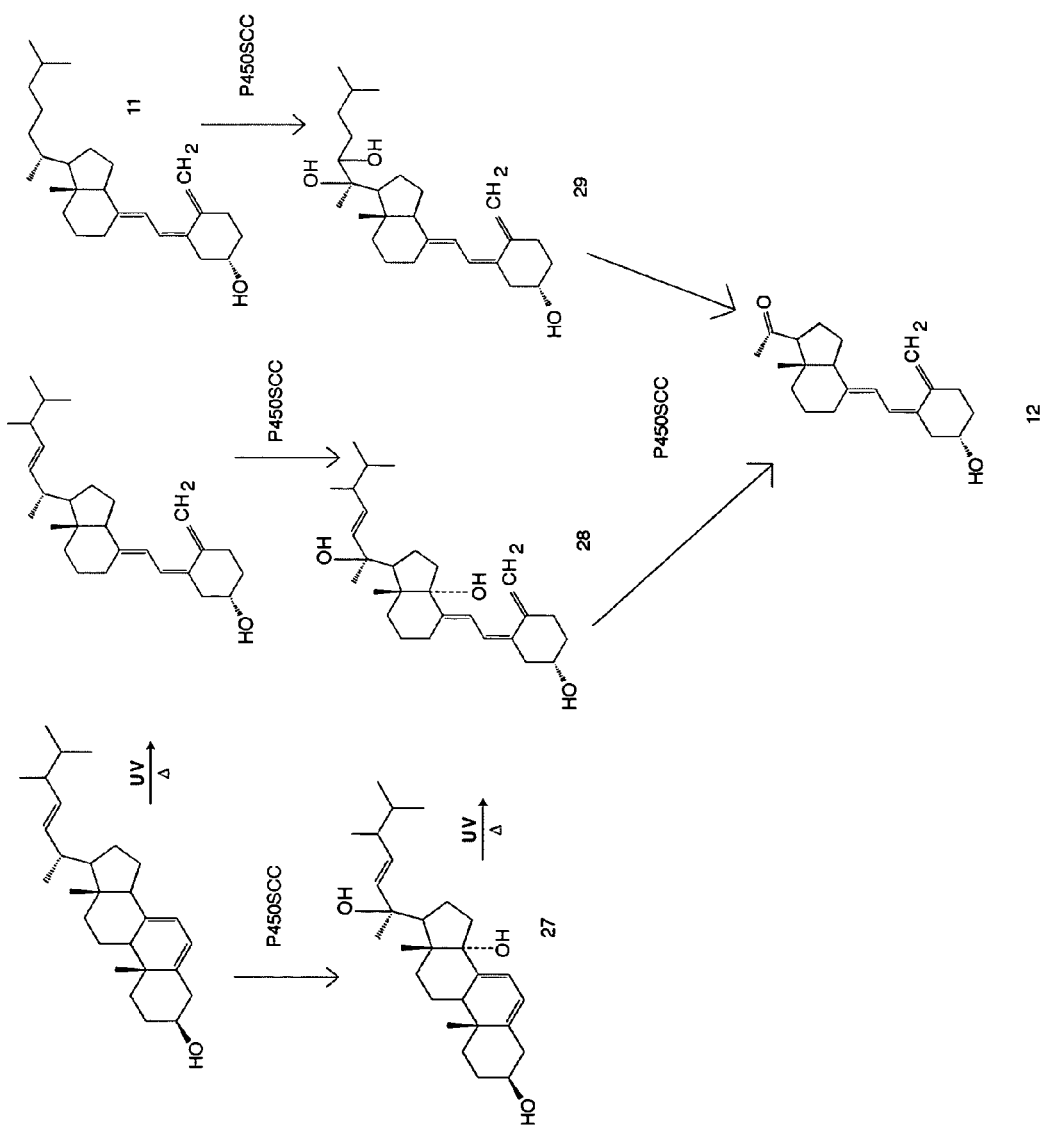

FIG. 1B depicts the 7-dehydropregnenolone enzyme conversion product 3-hydroxy-5,7-androstadiene-17-one (#21) and the following hydroxy and/or keto derivatives (#22-26) generated by the action of UVB radiation and/or subsequent chemical or enzymatic oxidation of the hydroxy groups:

22. 3β,17β-dihydroxy-5,7-androstadiene
23. 17β-hydroxyetiocalciferol
24. 17-ketoetiocalciferol
25. 3-keto-17β-hydroxyetiocalciferol
26. 3,17-diketoetiocalciferol FIG. 1C depicts the enzymatic conversion of ergosterol, vitamin D2 and vitamin D3 to hydroxylated precursors of the vitamin D3-like compound #12 shown in FIG. 1A. The dotted line attaching —OH to C14 is representative of a potential binding site for the second hydroxyl group.

Figure 2A:
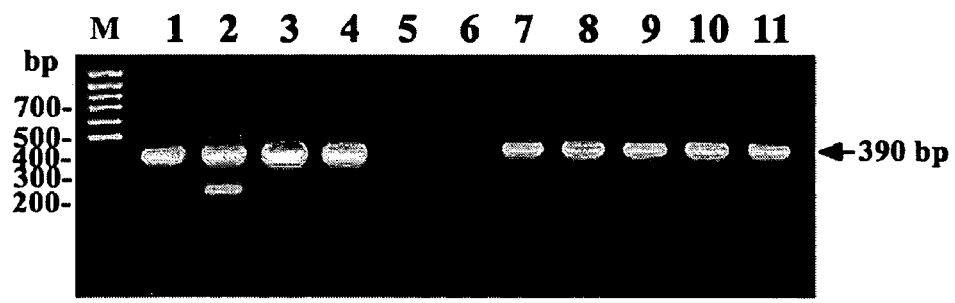
Figure 2B:
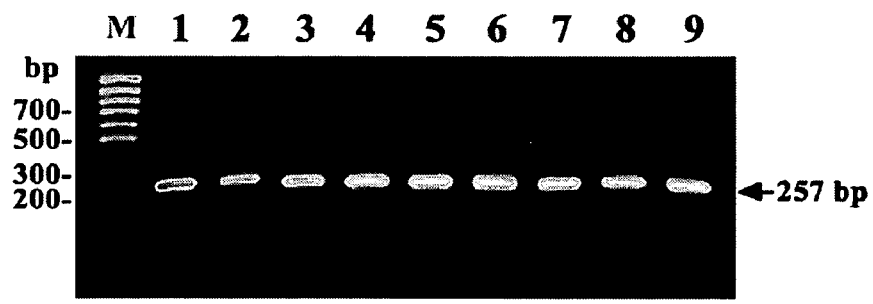
Figure 2C:
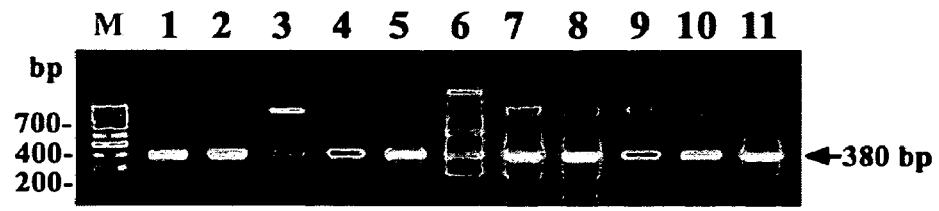
Figure 2D:
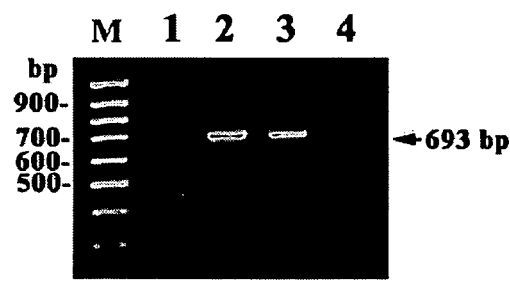
Figure 2E:
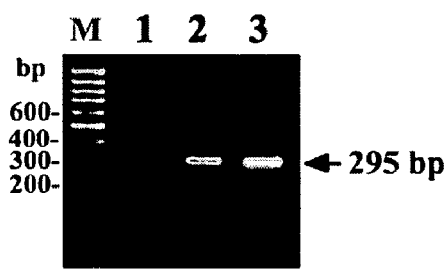
Figure 2F:
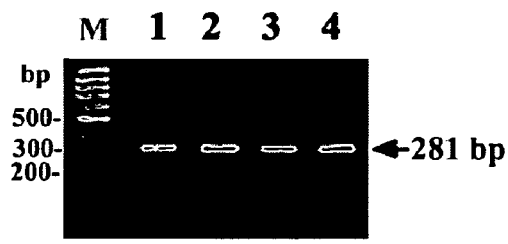

27. dihydroxyergosterol hydroxylated at least at C20
28. dihydroxyergocalciferol hydroxylated at least at C20
29. 20,22-dihydroxycholecalciferol FIGS. 2A-2F depict expression of P450scc (CYP11A1) (FIGS. 2A, 2D), adrenodoxin (FDX1) (FIGS. 2B, 2E) and adrenodoxin reductase (FDXR) genes (FIGS. 2C, 2F) in human and mouse skin using nested PCR. Human samples are shown in FIGS. 2A-2C and mouse samples are shown in samples in FIGS. 2D-2F. Arrows indicate the size of the amplified message. DNA ladder is marked M. FIG. 2A: HaCaT keratinocytes (lane 1); normal epidermal keratinocytes (lane 2); C1-4 squamous cell carcinoma (lane 3); dermal fibroblasts (lane 4); epidermal melanocytes (lane 5); melanoma lines SKMEL-188 (lane 6); SBCE2 (lane 7); WM35 (lane 8); WM98 (lane 9); WM164 (lane 10) and WM134D (lane 11). FIG. 2B: HaCaT keratinocytes (lane 1); normal epidermal keratinocytes (lane 2); dermal fibroblasts (lane 3); epidermal melanocytes (lane 4); C1-4 squamous cell carcinoma (lane 5); melanoma lines SKMEL-188 (lane 6); SBCE2 (lane 7); WM35 (lane 8); WM98 (lane 9). FIG. 2C: HaCaT keratinocytes (lane 1); normal epidermal keratinocytes (lane 2); C1-4 squamous cell carcinoma (lane 3); dermal fibroblasts (lane 4); epidermal melanocytes (lane 5); melanoma lines SKMEL-188 (lane 6); SBCE2 (lane 7); WM35 (lane 8); WM98 (lane 9); WM164 (lane 10) and WM134D (lane 11). FIGS. 2D &2F: pituitary (lane 1); anagen skin (lane 2); telogen skin (lane 3); and S91 melanoma (lane 4). FIG. 2E lanes: anagen skin (lane 1); telogen skin (lane 2); and S91 melanoma (lane 3).

Figure 3A:
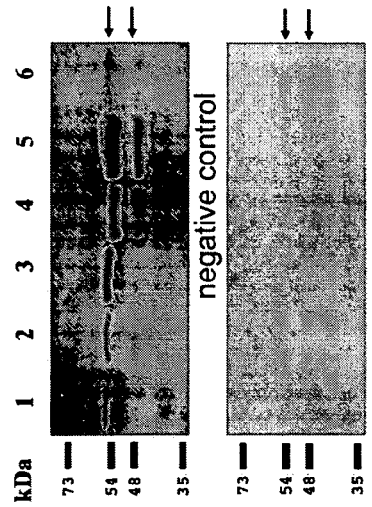
Figure 3B:
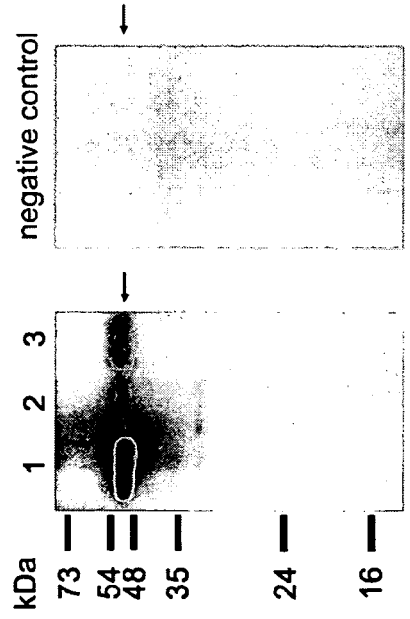
Figure 3C:
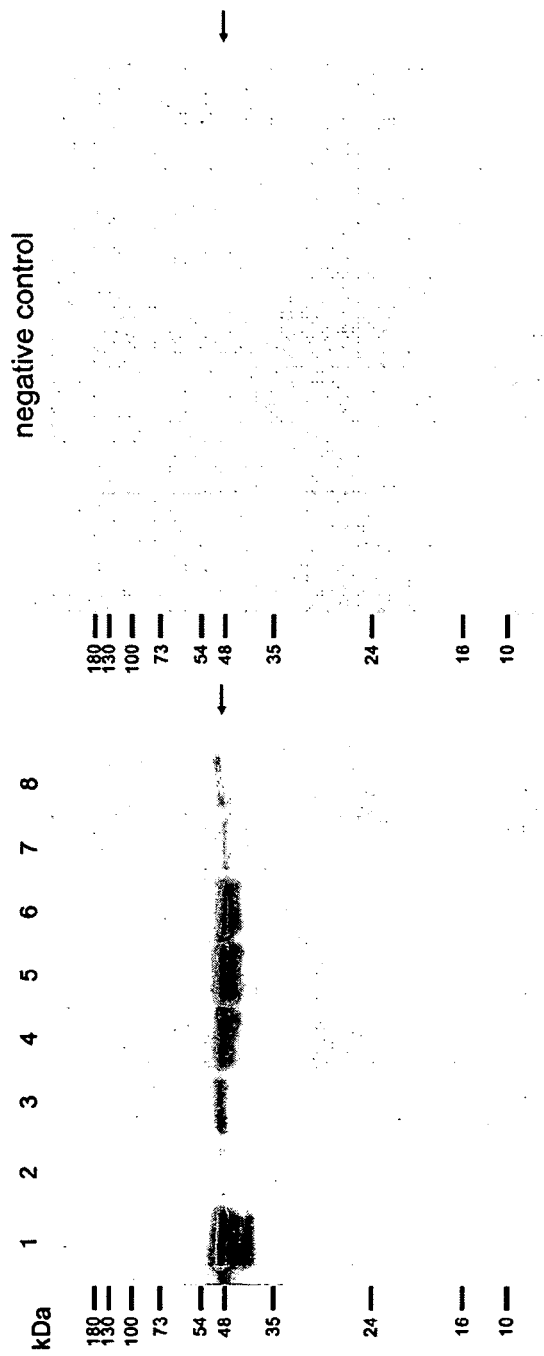

FIGS. 3A-3C demonstrate the expression of P450scc protein (FIGS. 3A-3B) and adrenodoxin reductase (FIG. 3C) in human skin. Shown are blots incubated with specific antibodies and controls with the primary antibody omitted. Size of molecular weight markers is on the left and arrows indicate immunoreactive proteins. FIG. 3A: placenta (lane 1); skin from white (lane 2) or black (lane 3) patients. FIG.

3B: HaCaT keratinocytes (lane 1); C1-4 squamous cell carcinoma (lane 2); dermal fibroblasts (lane 3); normal epidermal keratinocytes (lane 4); melanoma lines WM1341D (lane 5) and SBCE2 (lane 6). FIG. 3C lanes: placenta (lane 1); skin from white (lane 2) or black (lane 3) patients; melanoma WM35 (lane 4); normal epidermal keratinocytes (lane 5); HaCaT keratinocytes (lane 6); C1-4 squamous cell carcinoma (lane 7); dermal fibroblasts (lane 8).

Figure 4:
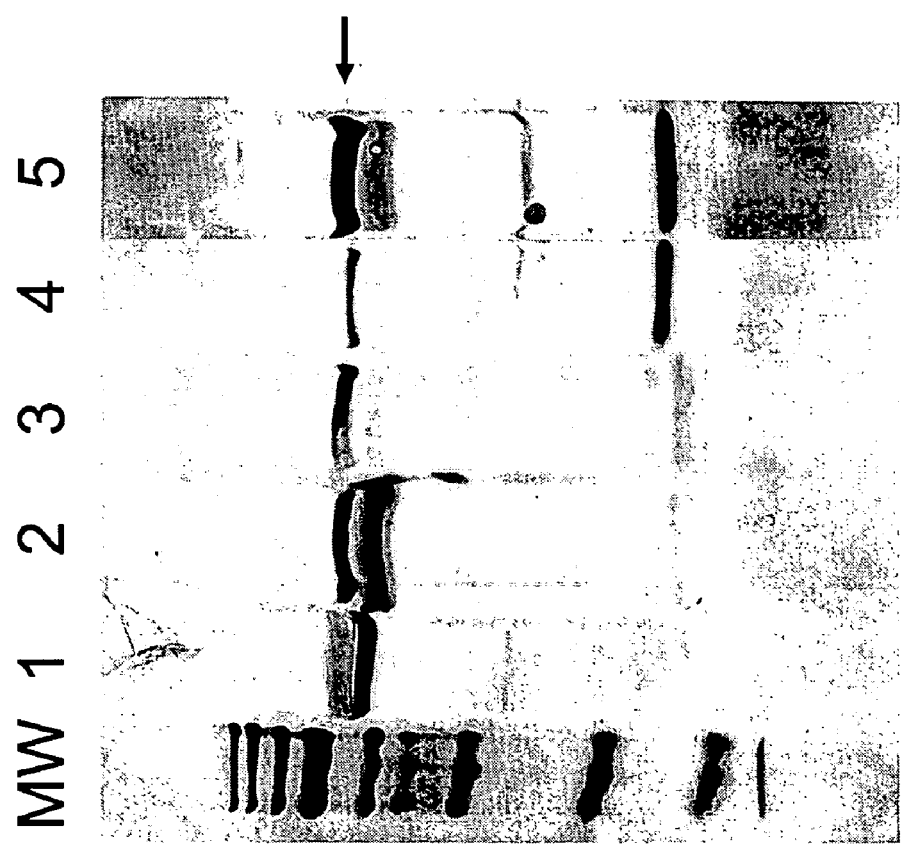
Figure 4:
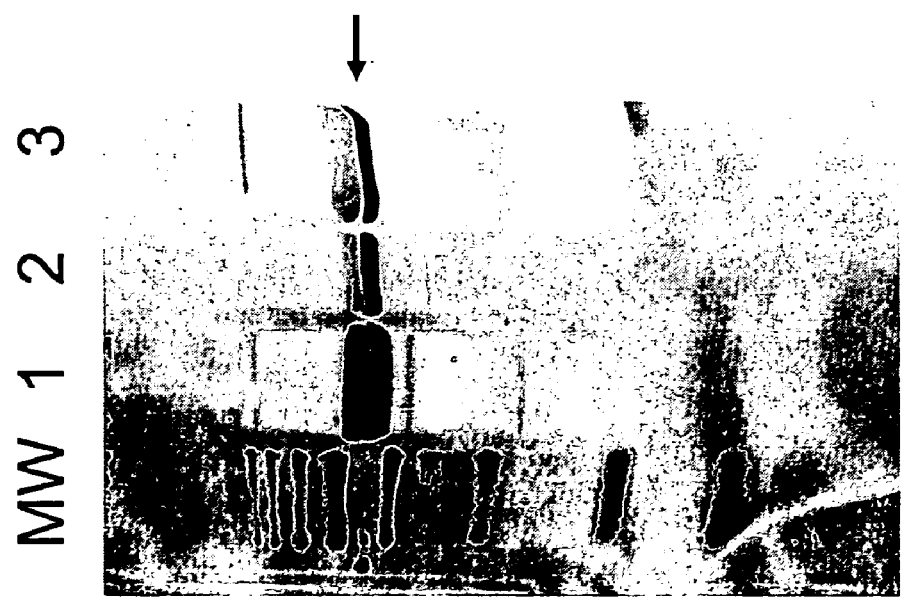

FIGS. 4A-4B demonstrate the expression of MLN64 protein (arrow) in human skin (FIG. 4A) and human and rodent skin cells (FIG. 4B). Molecular weight (MW) markers are 180, 130, 73, 54, 48, 35, 24, 16 and 10 kD. FIG. 4A: placenta (lanes 1-2); skin (lane 3). FIG. 4B: human SBCE2 (lane 1), WM35 (lane 2), hamster AbC-1 (lane 3) and mouse S-91 (lane 4) melanomas; placenta (lane 5).

Figure 5:
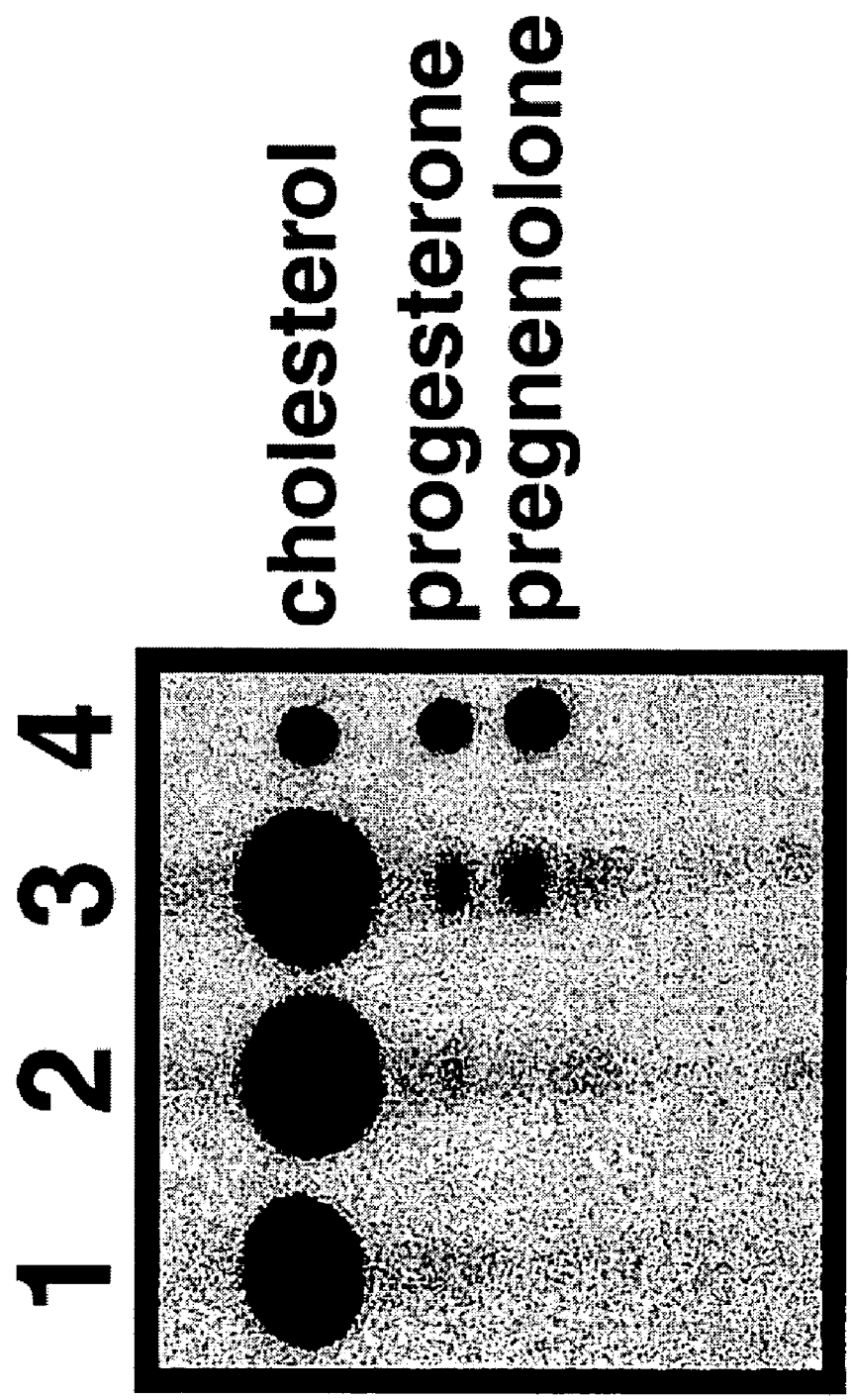

FIG. 5 demonstrates the side chain cleavage of radiolabeled cholesterol by mitochondria from skin cells. Purified [4-$^{14}$C] cholesterol prior to reaction is shown in lane 1 and the positions of authentic standards are marked in lane 4.

Figure 6A:
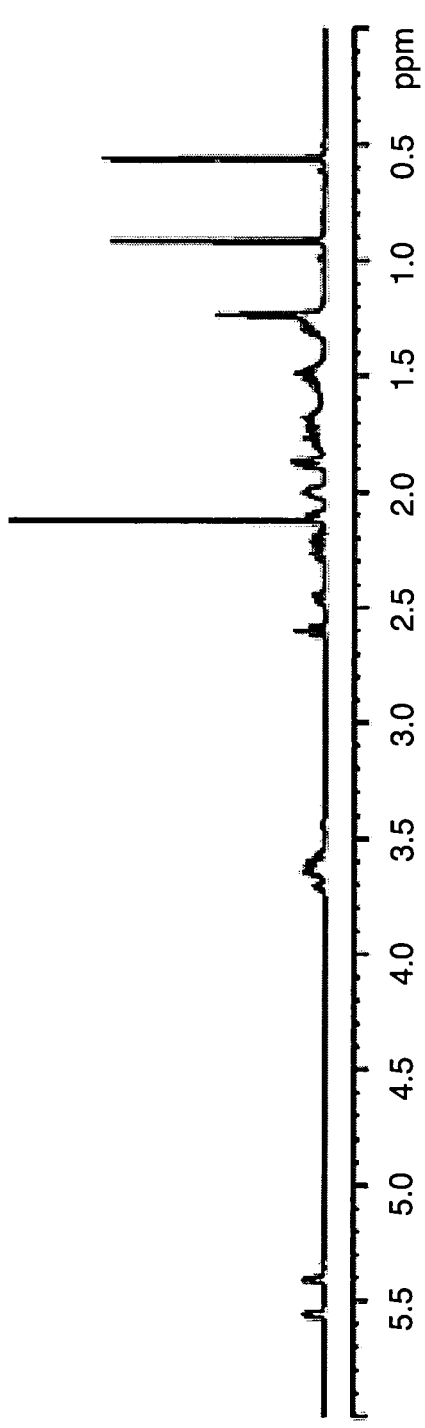
Figure 6B:
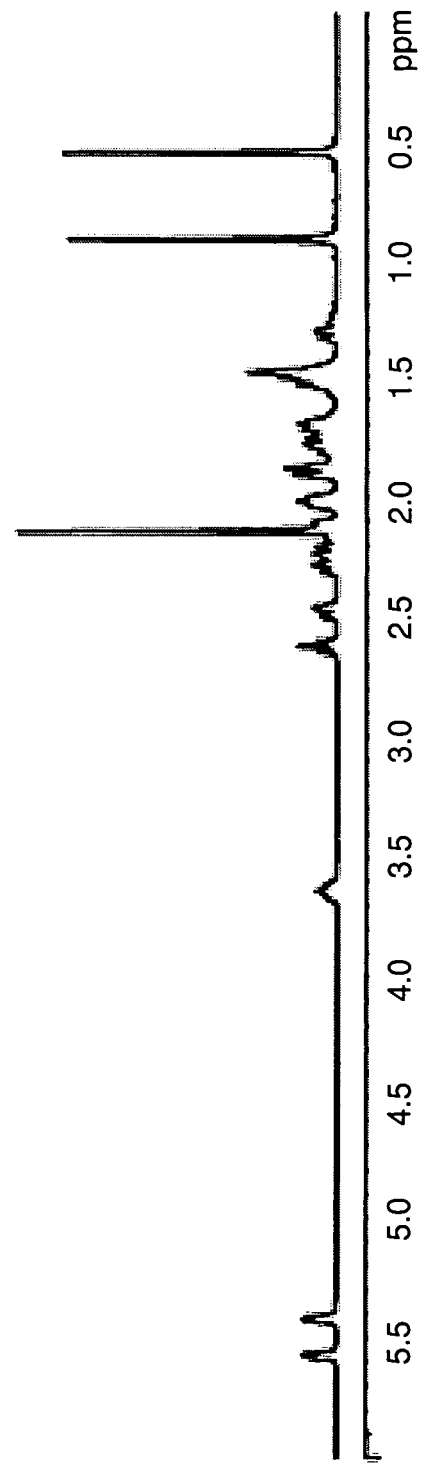

FIG. 6A-6B depict the $^1$H-NMR spectra of the product of P450scc-mediated enzymatic side chain cleavage of 7-DHC (FIG. 6A) and the 7-DHP synthetic standard (FIG. 6B).

Figure 7:
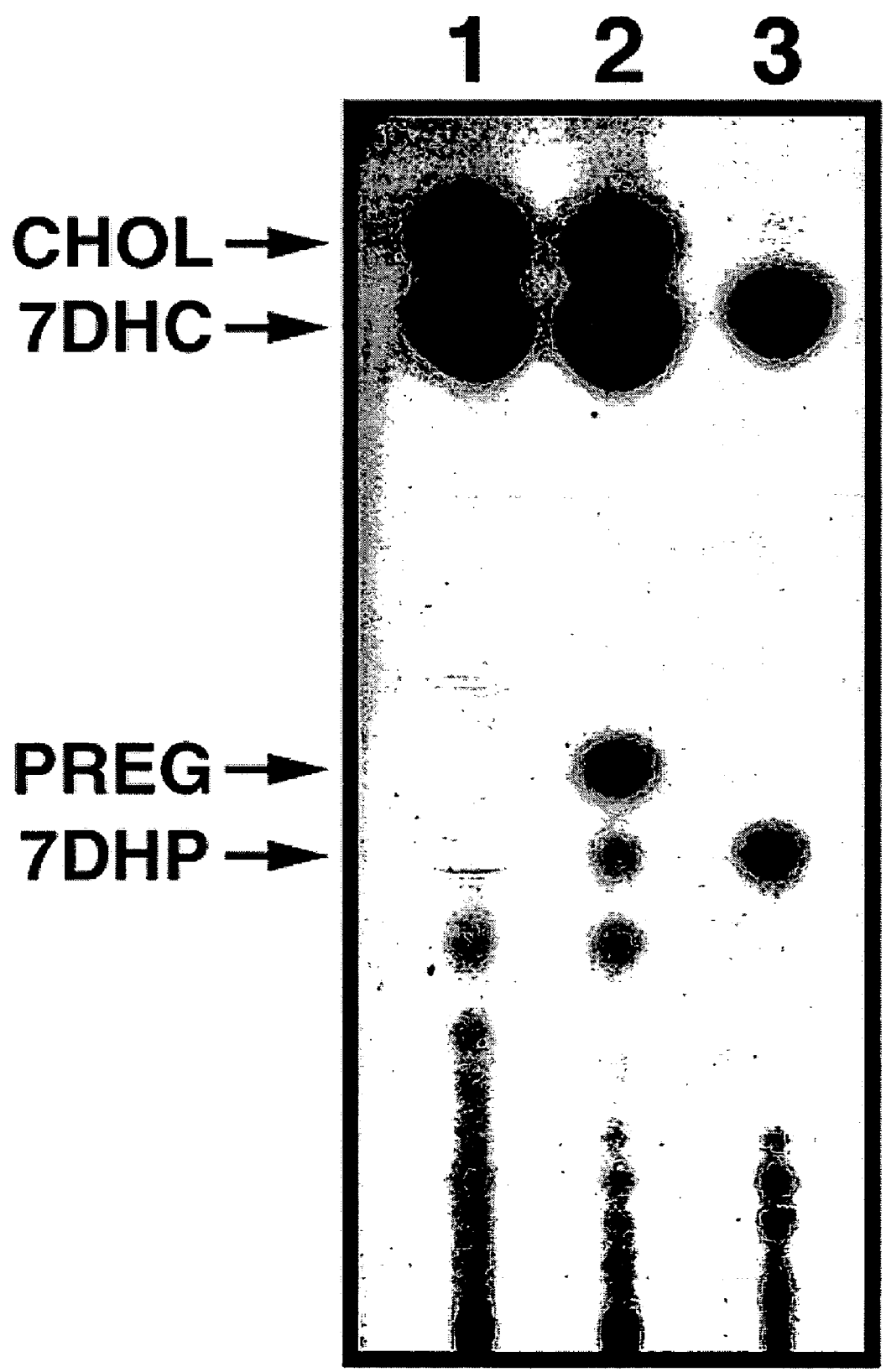

FIG. 7 demonstrates the conversion of 7-dehydrocholesterol to 7-dehydropregnenolone by mitochondria from the human placenta. Mitochondria, 1.4 mg/ml, were incubated with 200 µM 7-DHC, 5.0 µM N-62 StAR protein and 10 µM cyanoketone for 2 h at 37° C. Reaction products were analysed by TLC. Control incubation without NADPH and isocitrate (lane 1); experimental incubation with NADPH and isocitrate (lane 2); 7-DHC and 7-DHP standards (lane 3); cholesterol, 7-DHC, pregnenolone and 7-dehydropregnenolone are marked by arrows.

Figure 8A:
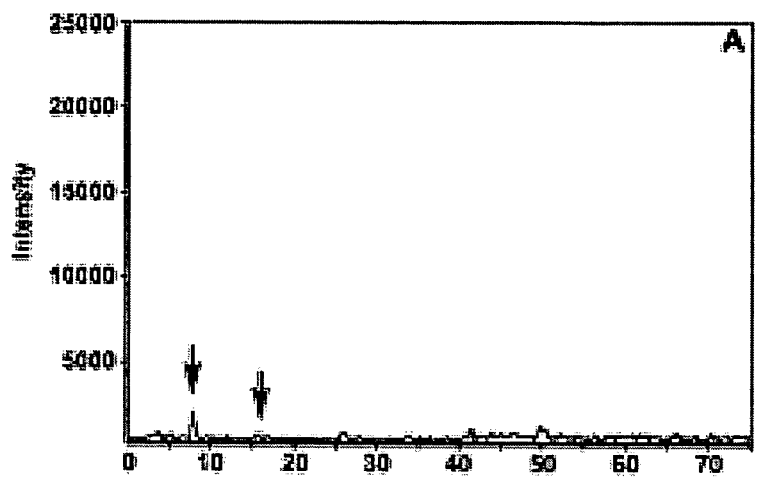
Figure 8B:
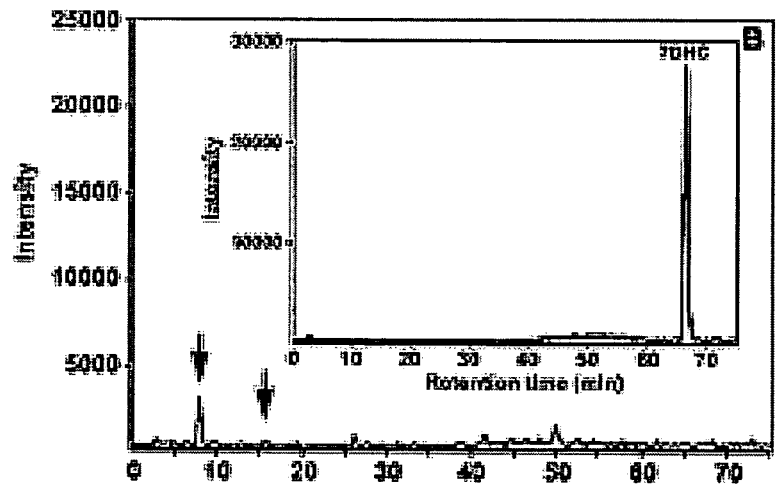
Figure 8C:
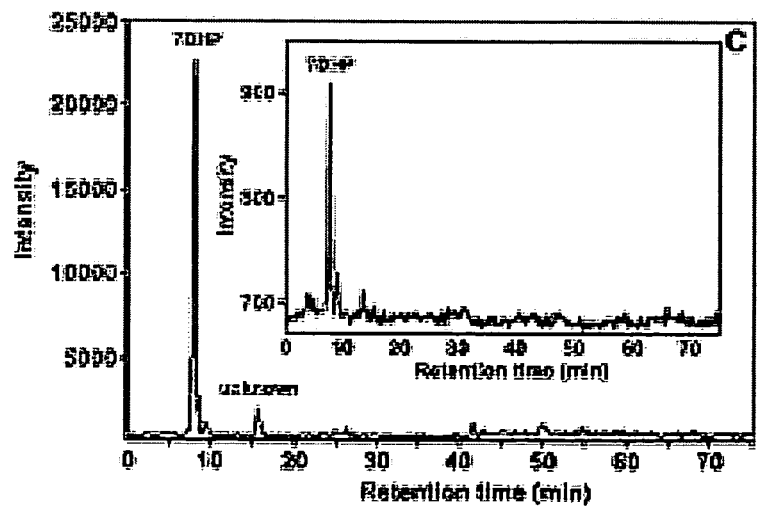
Figure 8D:
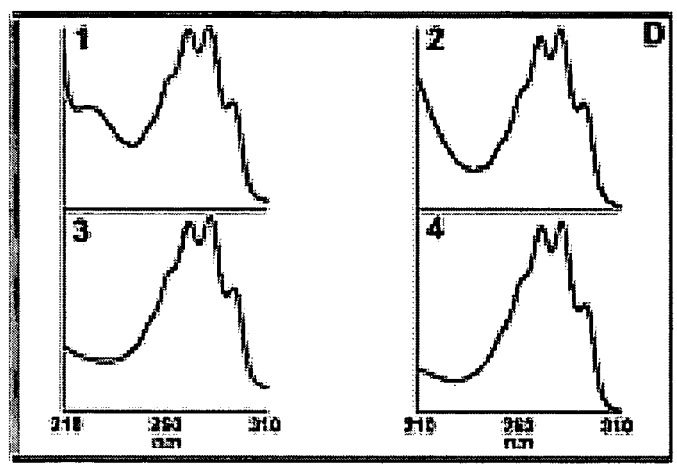
Figure 8E:
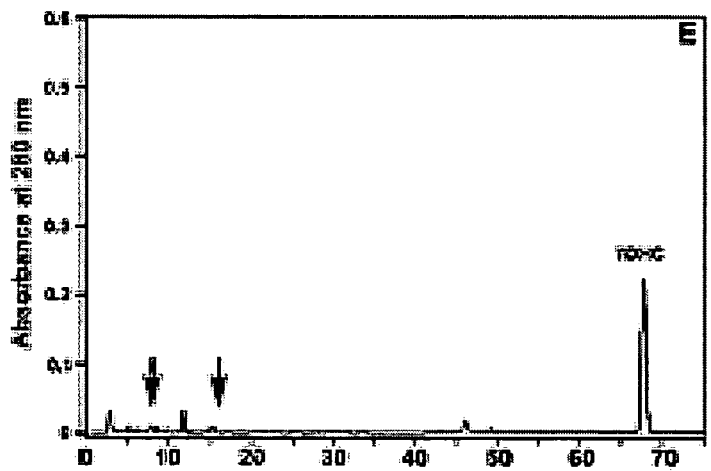
Figure 8F:
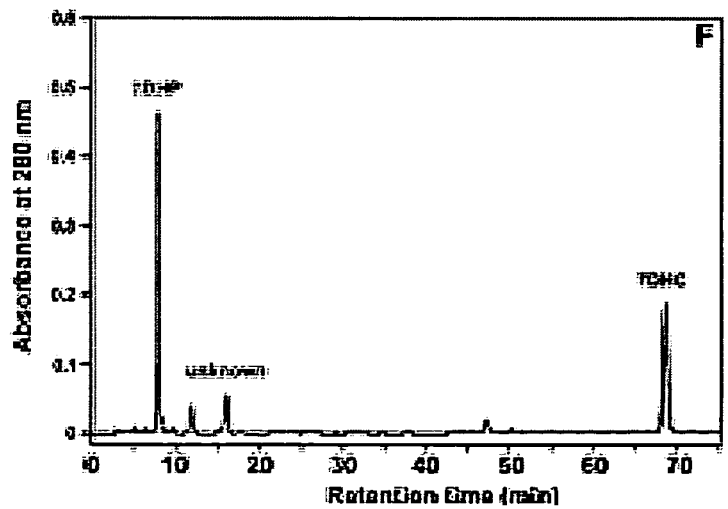

FIGS. 8A-8F show the conversion of 7-DHC into 7-DHP by rat adrenal mitochondria. Samples were analyzed by LC/MS (FIGS. 8A-8C) or LC with UV spectrophotometry (FIGS. 8D-8F). Mitochondria were incubated in the presence of (FIGS. 8C and 8F) and in the absence of, as controls, NADPH and isocitrate (FIGS. 8B and 8E).

Figure 9:
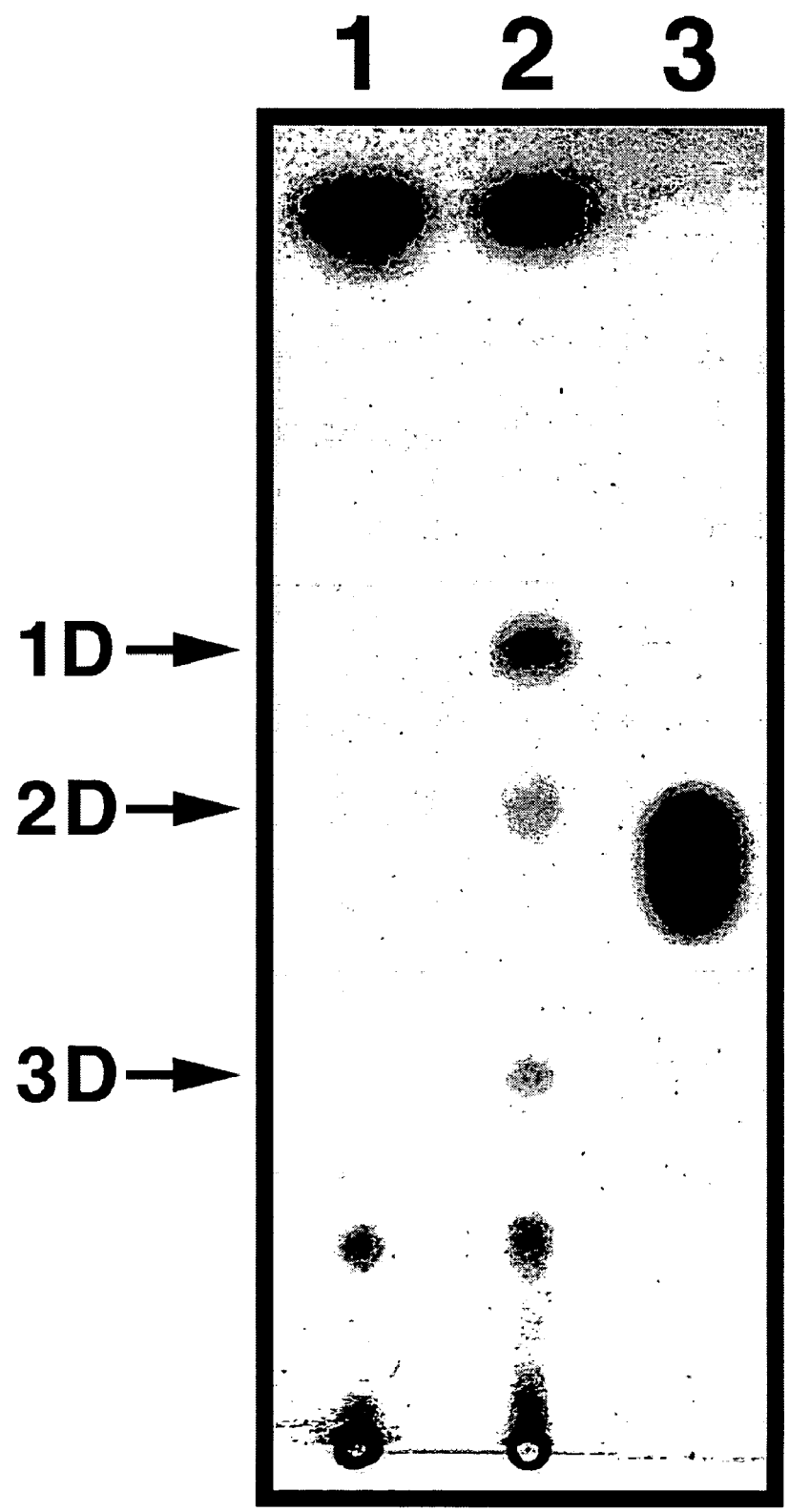

FIG. 9 demonstrates the conversion of vitamin D3 to vitamin D3-like products by purified bovine P450scc. Reaction products were analyzed by TLC. Control is incubation without NADPH and isocitrate (lane 1); experimental incubation with NADPH and isocitrate (lane 2); pregnenolone standard (lane 3). Products of vitamin D3 metabolism, D1, D2 and D3, are marked by arrows.

Figure 10:
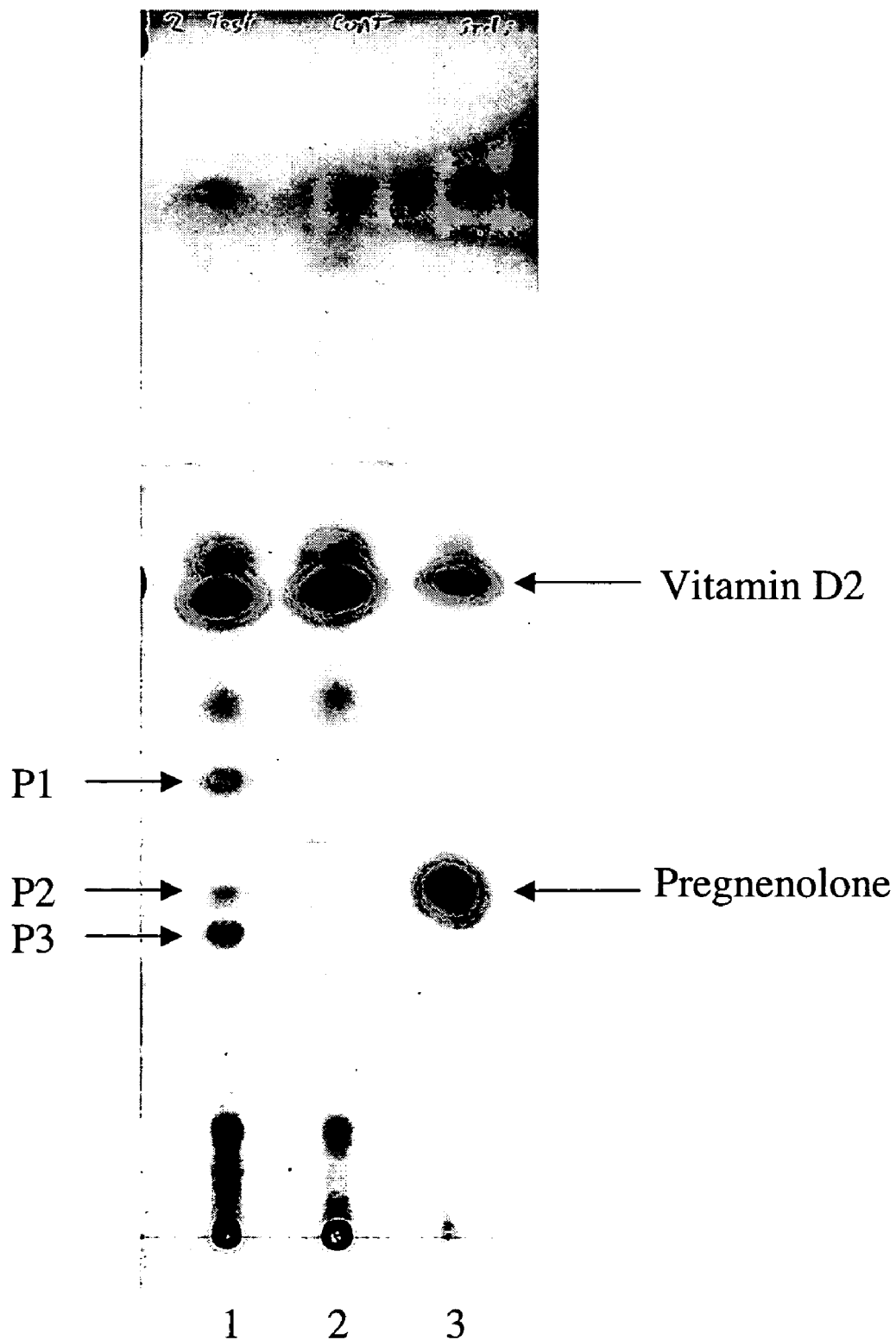

FIG. 10 shows the TLC separation of products of vitamin D2 transformation by cytochrome P450scc system. Lane 1: products P1, P3 and P2 corresponding to pregnenolone; Lane 2: control with no NADPH; Lane 3: Vitamin D2 and pregnenolone standards.

Figure 11A:
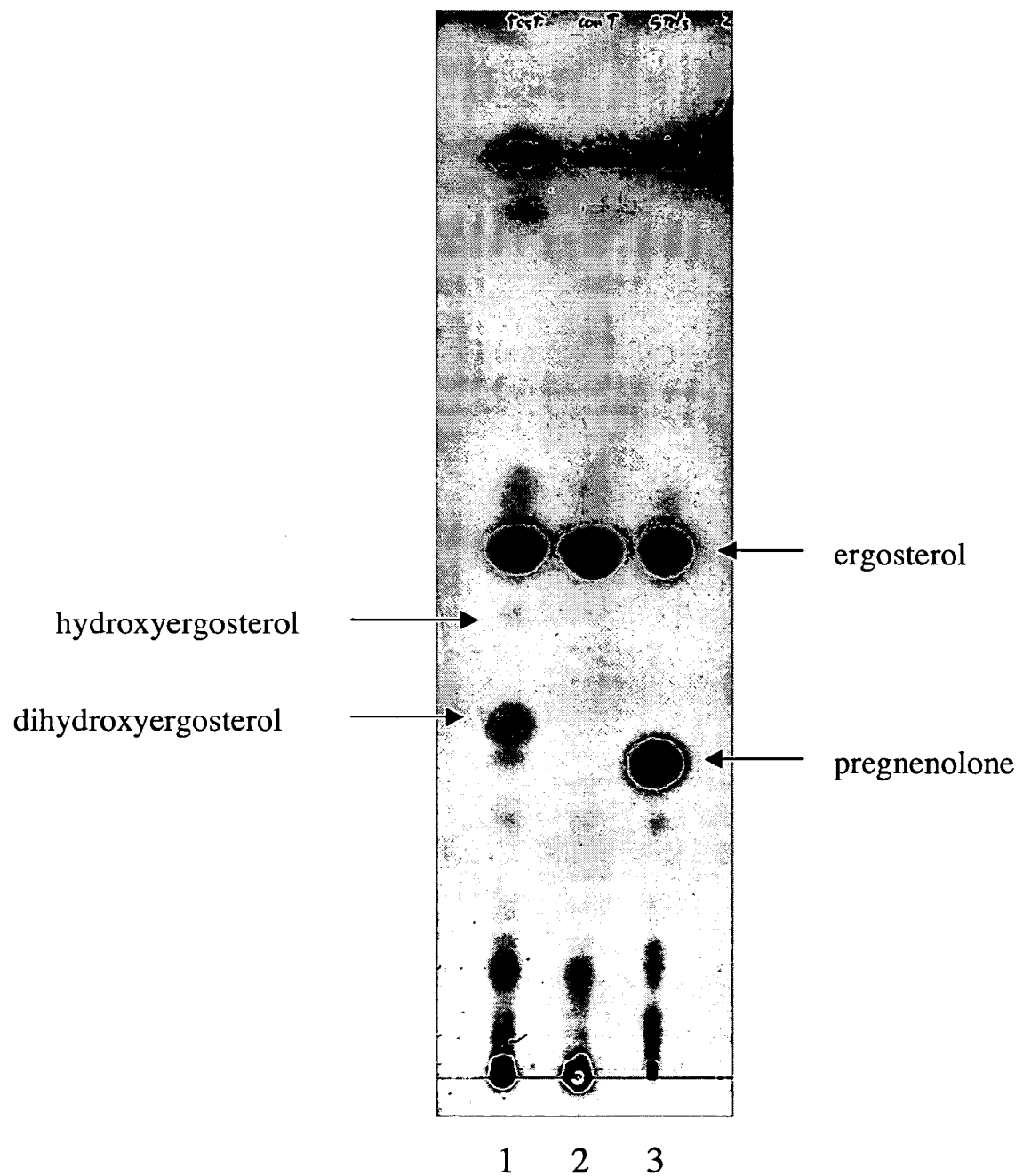
Figure 11C:
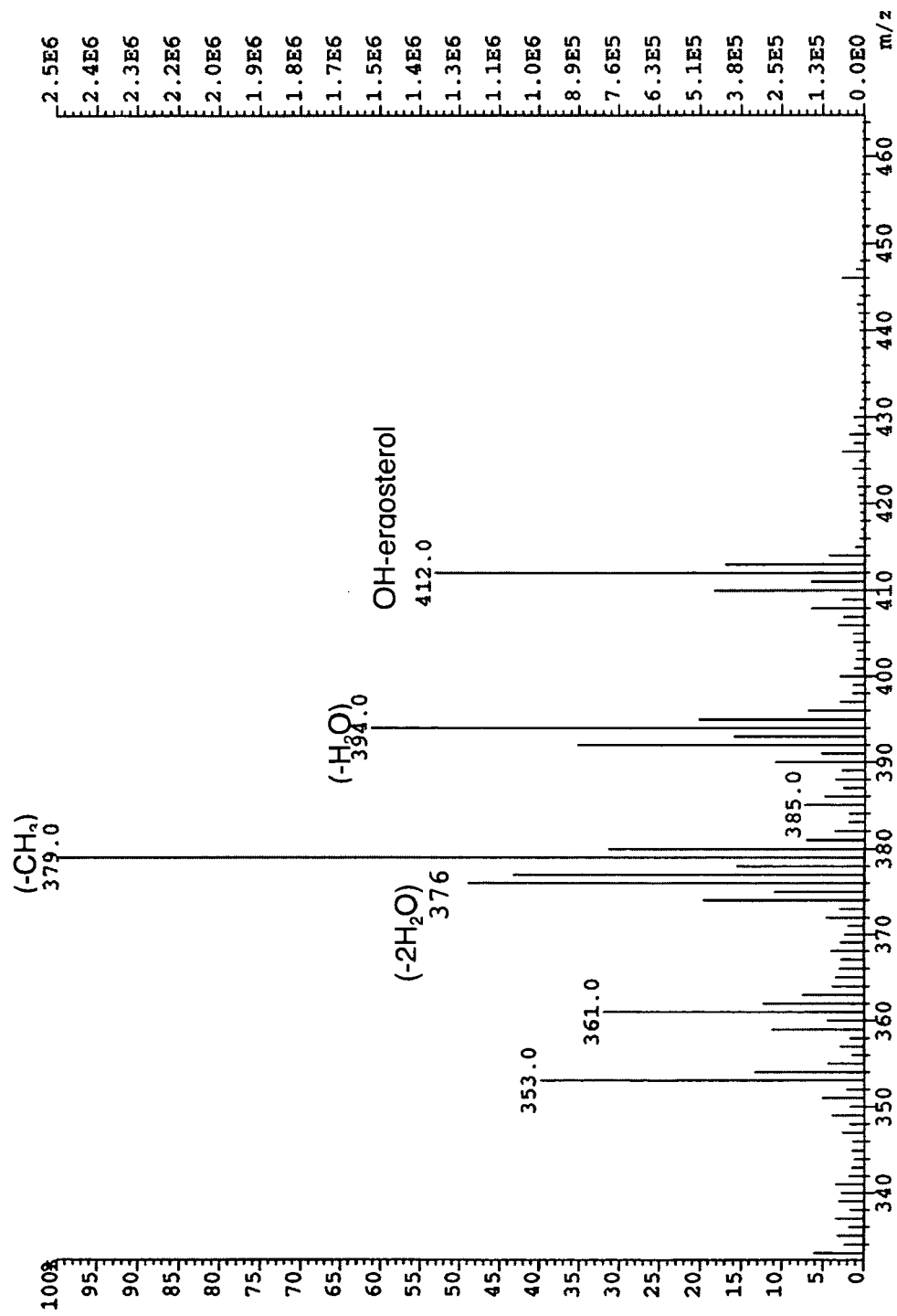

FIGS. 11A-11C show the TLC separation and mass spectrometry spectra of products of ergosterol transformation by cytochrome P450scc system. FIG. 11A identifies metabolic products hydroxyergosterol and dihydroxyergosterol in lane 1 with control no P450scc in lane 2 and standards in lane 3. FIG. 11B is the mass spectrometry spectra of the product identified as dihydroxyergosterol in FIG. 11A confirming the correct mass for dihydroxyergosterol (428). FIG. 11C is the mass spectrometry spectra of the product identified as hydroxyergosterol on FIG. 11A confirming the correct mass for dihydroxyergosterol (412) with its degradation products (—H20)=394 (—H20—CH3)=379 and (-2H20)=376.

DETAILED DESCRIPTION OF THE INVENTION

One embodiment of the present invention provides a method of producing 7-dehydropregnenolone, comprising enzymatically shortening a C17 side chain of 7-dehydrocholesterol via a cytochrome P450scc enzyme system to produce 7-dehydropregnenolone. In all aspects of this embodiment the P450scc enzyme system may be an in vitro system comprising cytochrome P450scc enzyme, adrenodoxin, adrenodoxin reductase, and NADPH. The P450scc enzyme system further may comprise a detergent or a phospholipid. In the NADPH may be generated within the enzyme system.

In an aspect of this embodiment, the method further produces a vitamin D3-like compound where the method comprises thermophotolytically breaking a C9-C10 bond in 7-dehydropregnenolone via UVB radiation; and converting 7-dehydropregnenolone to the vitamin D3-like compound via thermal intramolecular rearrangement around the broken bond. An example of the vitamin D3-like compound is 5Z,7E-3β-hydroxy-9,10-secopregna-5,7,10(19)trien-20-one In another aspect to this embodiment, the method further produces a hydroxy derivative of 7-dehydropregnenolone where the method comprises enzymatically hydroxylating 7-dehydropregnenolone in at least one position. In this further embodiment 7-dehydropregnenolone maybe hydroxylated via a P450cc11 enzyme, a P450c17 enzyme, a P450c21 enzyme, or 20-hydroxysteroid dehydrogenase or a combination thereof. Examples of 7-dehydropregnenolone hydroxy derivatives are 7-dehydropregnenolone hydroxy derivative is 3β,11α-dihydroxypregna-5,7-dien-20-one, 3β,11β-dihydroxypregna-5,7-dien-20-one, 3β,17β-dihydroxypregna-5,7dien-20-one, 3β,21-dihydroxypregna-5,7-dien-20-one, 3β,17β,21-trihydroxypregna-5,7-dien-20-one, 3β,11α,17β-trihydroxypregna-5,7-dien-20-one, 3β,11β,17β-trihydroxy pregna-5,7-dien-20-one, 3β,11α,21-trihydroxypregna-5,7-dien-20-one, 3β,11β,21-trihydroxy pregna-5,7-dien-20-one, 3β,11α,17β,21-tetrahydroxypregna-5,7-dien-20-on or 3β,11β,17β,21-tetrahydroxy pregna-5,7-dien-20-one, 3β,20α-dihydroxypregna-5,7-diene or 3β,20β-dihydroxypregna-5,7-diene.

Further to this aspect the method produces an hydroxy derivative of a vitamin D3-like compound where the method comprises thermophotolytically breaking a C9-C10 bond in the 7-dehydro pregnenolone hydroxy derivative via UVB radiation and converting the hydroxy derivative to the vitamin D3-like compound derivative via thermal intramolecular rearrangement around the broken bond. Examples of the vitamin D3-like hydroxy derivative are 5Z,7E-3β,11α-dihydroxy-9,10-secopregna-5,7,10(19)trien-20-one, 5Z,7E-3β,11β-dihydroxy-9,10-secopregna-5,7,10(19)trien-20-one, 5Z,7E-3,17β-dihydroxy-9,10-secopregna-5,7,10(19)trien-20-one, 5Z,7E-3,β,21-dihydroxy-9,10-secopregna-5,7,10 (19)trien-20-one, 5Z,7E-3β,17β,21-trihydroxy-9,10-secopregna-5,7,10(19)trien-20-one, 5Z,7E-3β,11α,17β-trihydroxy-9,10-secopregna-5,7,10(19)trien-20-one, 5Z7E-3β,11β,17β-trihydroxy-9,10-secopregna-5,7,10(19) trien-20-one, 5Z,7E-3β,11α,21-trihydroxy-9,10-secopregna-5,7,10(19) trien-20-one, 5Z,7E-3β,11β,21-trihydroxy-9,10-secopregna-5,7,10(19)trien-20-one, 5Z,7E-3β,11α,17β,21- tetrahydroxy-9,10-secopregna-5,7,10(19)trien-20-one, 5Z,7E-3β,11β,17β,21-tetrahydroxy-9,10-secopregna-5,7,10 (19)trien-20-one, 5Z,7E-3β,20α-dihydroxy-9,10-secopregna-5,7,10(19)triene or 5Z,7E-3β,20β-dihydroxy-9,10-secopregna-5,7,10(19)triene.

In yet another aspect of this embodiment the method further produces an androstadiene-like compound where the method comprises enzymatically converting 7-dehydroprognenolone via P450c17 to 3-hydroxy-5,7-androstadiene-17-one or 3,17-dihydroxy-5,7-androstadiene. Further to this aspect the method produces a vitamin D3-like compound where the method comprises hermophotolytically breaking a C9-C10 bond in the 3-hydroxy-5,7-androstadiene-17-one or 3,17-dihydroxy-5,7-androstadiene via UVB radiation; and converting the androstadienes to said vitamin D3-like compound via thermal intramolecular rearrangement around said broken bond. Examples of an androstadiene are 17-ketoetiocalciferol or 17β-etiocalciferol. Further still to this aspect the method comprises enzymatically or chemically oxidizing an hydroxy group present at C3, C17 or a combination thereof on said vitamin D3-like compound. Examples of these oxidized compounds are 3-keto-17-hydroxyetiocalciferol or 3,17-diketoetiocalciferol.

In a related embodiment there is provided a method of producing a vitamin D3-like compound, enzymatically hydroxylating at least a C17 side chain of ergosterol, vitamin D2, vitamin D3 or a combination thereof via a cytochrome P450scc enzyme system and, wherein ergosterol is hydroxylated, optionally, thermophotolytically converting the hydroxylated ergosterol to the C17 hydroxylated vitamin D2 via UVB radiation and thermal intramolecular rearrangement at C9-C10; and enzymatically shortening the hydroxylated C17 side chain via the cytochrome P450scc enzyme system and, wherein the C17 side chain is shortened on the hydroxylated ergosterol, thermophotolytically converting the ergosterol via UVB radiation and thermal intramolecular rearrangement at C9-C10.

In one aspect the C17 side chain is hydroxylated at least at position C20 within the chain. In a related aspect the C17 side chain comprises vitamin D3 and is hydroxylated at positions C20 and C22. In all aspects of this embodiment the vitamin D3-like compound may be 5Z,7E-3β-hydroxy-9,10-secopregna-5,7,10(19)trien-20-one. The P450scc enzyme system is as described supra. Related to these aspects there are provided ergosterol derivatives and vitamin D2 derivatives produced by the cytochrome P450scc enzyme system described supra that are hydroxylated at least at position C20 within the C17 side chain.

Further to this embodiment the method produces derivatives of the vitamin D3-like compounds where the method comprises enzymatically hydroxylating the vitamin D3-like compound in at least one position. The vitamin D3-like hydroxy derivatives are as described supra. The enzymes utilized to hydroxylate the vitamin D3-like compound are as described supra.

In another embodiment of the present invention, there is provided a compound having the chemical structure of:

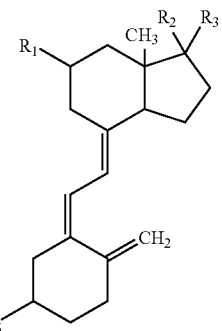

wherein $R_1$ is hydrogen or —OH; $R_2$ is —CH($R_4$)—CH$_2$ ($R_5$) and $R_3$ is hydrogen or —OH; or $R_2$ and $R_3$ form a carbonyl group with C20; $R_5$ is hydrogen or —OH; and $R_6$ is —OH or forms a carbonyl group with C3. These compounds may be 5Z,7E-3β,11α-dihydroxy-9,10-secopregna-5,7,10(19)trien-20-one, 5Z,7E-3β,11β-dihydroxy-9,10-secopregna-5,7,10(19)trien-20-one, 5Z,7E-3,17β-dihydroxy-9,10-secopregna-5,7,10(19)trien-20-one 5Z,7E-3β,21-dihydroxy-9,10-secopregna-5,7,10(19)trien-20-one, 5Z,7E-3β,17β,21-trihydroxy-9,10-secopregna-5,7,10(19)trien-20-one, 5Z,7E-3β,11α,17β-trihydroxy-9,10-secopregna-5,7,10(19)trien-20-one, 5Z,7E-3β,11β,17β-trihydroxy-9,10-secopregna-5,7,10(19)trien-20-one, 5Z,7E-3β,11α,21-trihydroxy-9,10-secopregna-5,7,10(19)trien-20-one, 5Z,7E-3β,11β,21-trihydroxy-9,10-secopregna-5,7,10(19)trien-20-one, 5Z,7E-3β,11α,17β,21-tetrahydroxy-9,10-secopregna-5,7,10(19)trien-20-one, 5Z,7E-3β,17β,21-tetrahydroxy-9,10-secopregna-5,7,10(19)trien-20-one, 5Z,7E-3β,20α-dihydroxy-9,10-secopregna-5,7,10(19)triene, 5Z,7E-3β,20β-dihydroxy-9,10-secopregna-5,7,10(19)triene, 17-ketoetiocalciferol, 17β-etiocalciferol, 3-keto-17-hydroxyetiocalciferol or 3,17-diketoetiocalciferol.

In one aspect of this embodiment the compounds may be derivatives of a vitamin D3-like compound where $R_2$ is —CH($R_4$)—CH$_2$($R_5$); $R_1$, $R_3$, and $R_5$ are independe hydrogen or hydroxy such that at least one of $R_1$, $R_3$ or $R_5$ is hydroxy; $R_4$ is a carbonyl bond formed with C20; and $R_6$ is —OH; or $R_1$, $R_3$, and $R_5$ are hydrogen; and $R_4$ and $R_6$ are hydroxy. Examples of these vitamin D3-like derivatives are as discussed supra.

In another aspect of this embodiment the compounds may be derivatized androstadienes or vitamin D2-like compounds or derivatives where $R_1$ is hydrogen; R2 is hydrogen; R3 is hydroxy; or $R_2$ and $R_3$ form a carbonyl group with C17; and $R_6$ is —OH or forms a carbonyl group with C3. Examples of these derivatives are as discussed supra.

The following abbreviations are used herein: 7-DHC: 7-dehydrocholesterol; 7-DHP: 7-dehydropregnenolone; vitDL: vitamin D2-like or D3-like compound; 20-HSD: 20-hydroxysteroid dehydrogenase; PL: phospholipid.

Provided herein are methods for using 7-dehydrocholesterol, vitamin D3 or vitamin D2 as substrates for cytochrome P450scc enzyme to generate steroid compounds, such as, 7-dehydropregnenolone, vitamin D3-like and vitamin D2-like compounds, respectively. The genes and proteins required for the P450scc system are expressed concomitantly in the skin and skin cells. 7-dehydrocholesterol is readily available in human skin and as a natural substrate for P450scc has its C17 side chain shortened via enzymatic action to form 7-dehydropregnenolone. Alternatively, whether originating from local synthesis or from delivery to the skin by circulation, 5,7-steroidal dienes, e.g., 7-dehydropregnenolone and its hydroxy derivatives, directly can undergo UVB-induced thermal intramolecular rearrangement to vitamin D3-like compounds (vitDL).

Also provided are hydroxy derivatives of 7-dehydropregnenolone generated via the action of P450scc related enzymes P450c17, P450c21 and P450c11. These enzymes generate the derivatives 17-, 21- and 11-hydroxy 7-DHP. The C20 ketone may be reduced by the 20 hydroxysteroid dehydrogenase (20HSD) (31-32) to produce 20-OH-7-dehydropregnenolone. Again, since in the skin the unsaturated B ring of 7-DHP is prone to breakage by UVB of its 9,10-carbon bond with further thermal conversion into vitamin D3 (4) or vitDL (27), analogous cutaneous UVB photolytic transformations of 7-dehydropregnenolone hydroxylderivatives generates novel vitDL derivatives. Substrates for these light induced conversions, besides a local origin, could also be delivered to the skin from systemic circulation. FIG. 1A depicts the enzymatic pathways and steroid products described herein.

7-dehydropregnenolone is hydroxylated via P450c17, P450c21 and P450c11 to form 3β,11α-Dihydroxypregna-5,7-dien-20-one, 3β,11β-Dihydroxypregna-5,7-dien-20-one, 3β,17β-Dihydroxypregna-5,7-dien-20-one, 3β,21-Dihydroxypregna-5,7-dien-20-one, 3β,17β,21-Trihydroxypregna-5,7-dien-20-one, 3β,11α,17β,21-Tetrahydroxypregna-5,7-dien-20-one or 3β,11β,17β,21-Tetrahydroxypregna-5,7-dien-20-one. Alternatively, 7-dehydropregnenolone may be hydroxylated via 20 HSD to form 3β,20α-Dihydroxypregna-5,7-diene or 3β,20β-Dihydroxypregna-5,7-diene.

These 7-dehydropregnenolone hydroxy derivatives via thermophotolytic transformation produce 5Z,7E-3β,11α-dihydroxy-9,10-secopregna-5,7,10(19)trien-20-one, 5Z,7E-3β,11β-dihydroxy-9,10-secopregna-5,7,10(19)trien-20-one, 5Z,7E-3,17β-dihydroxy-9,10-secopregna-5,7,10(19)trien-20-one, 5Z,7E-3,β,21-dihydroxy-9,10-secopregna -5,7,10 (19)trien-20-one, 5Z,7E-3β,17β,21-trihydroxy-9,10-secopregna-5,7,10(19)trien-20-one, 5Z,7E-3β,11α17β,21-tetrahydroxy-9,10-secopregna-5,7,10(19) trien-20-one, 5Z,7E-3β,11β,17β,21-tetrahydroxy-9,10-secopregna-5,7,10 (19) trien-20-one, 5Z,7E-3β,11α-dihydroxy-9,10-secopregna-5,7,10(19)triene or 5Z,7E-3β,11rβ-dihydroxy-9,10-secopregna-5,7,10(19)triene. An example of a vitDL compound generated from either 7-dehydropregnenolone or vitamin D3 is 5Z,7E-3β-hydroxy-9,10-secopregna-5,7,10 (19)trien-20-one.

Additionally, P450c17 has high lyase activity with pregnenolone as substrate leading to production of some DHEA after C17-α hydroxylation. It is therefore contemplated that this enzyme acting on 7-dehydropregnenolone, which will enter the delta 5 pathway, leads to the enzymatic production of androstadiene-like compounds, such as, but not limited to, 3,17-dihydroxy-5,7-androstadiene or 3-hydroxy-5,7-androstadiene-17-one. Alternatively, 3,17-dihydroxy-5,7-androstadiene may be chemically oxidized to form 3-hydroxy-5,7-androstadiene-17-one. Production of both 17-hydroxy-7-DHP and 7-dehydro DHEA was reported in SLOS patients (18,46). This reaction may also undergo in the skin since it expresses CYP17 (10).

After exposure of the C19 dienes to UVB, the B ring is opened and the compound undergoes further thermolytic transformation to vitamin D3-like derivatives 17-ketoetiocalciferol and 17β-hydroxyetiocalciferol (FIG. 1B). Hydroxy groups at positions C3 and C17 can be further enzymatically or chemically oxidized (FIG. 1B). These oxidized derivatives are 3-keto-17-hydroxyetiocalciferol, and 3,17-diketoetiocalciferol. For example, cleavage of the C17-C20 bond by P450c17 directly produces a ketone group at position C17. The 17-hydroxy derivative subsequently is formed by 17-hydroxysteroid dehydrogenase enzyme.

Alternatively, the vitamin D3-like compounds may be produced enzymatically from ergosterol, vitamin D2 or vitamin D3 (FIG. 1C). The cytochrome P450scc enzyme system hydroxlates ergosterol, vitamin D2 or vitamin D3 at least within the C17 side chain where the hydroxylated C17 side chain subsequently is shortened to form the vitamin D3-like compound. Optionally, the hydroxylated ergosterol may be further thermophotolytically converted to the hydroxylated vitamin D2 via UVB radiation and thermal intramolecular rearrangement at the C9-C10 bond analogous to production of vitamin D3 from 7-dehydrocholesterol. Alternatively, the hydroxylated ergosterol may undergo enzymatic shortening of the C17 side chain and then undergo the thermophotolytic conversion at C9-C10 as described.

It is contemplated that the C17 side chains may be hydroxylated at least at position C20 within the chain by the P450scc enzyme system. Vitamin D3 may be hydroxylated at both C20 and C22 within the C17 chain. Furthermore, the P450c11, P450c17, P450c21, and 20 hydroxysteroid dehydrogenase enzymes may further hydroxylate the vitamin D3-like compounds to produce hydroxy derivatives described herein.

It is contemplated that the methods described herein readily can be used for large-scale industrial production of 7-dehydropregnenolone, hydroxy derivatives thereof and vitamin D2-like or D3-like compounds and derivatives thereof or precursors thereto or other molecules with new functions. The proteins, cytochrome P450scc, adrenodoxin reductase and adrenodoxin, may be purified from animal tissues, such as the bovine adrenal cortex, or expressed in bacteria transformed with plasmids containing cDNA encoding them. Proteins from animal tissues or expressed in bacteria may be purified by procedures including detergent extraction, hydrophobic chromatography, affinity chromatography or ion exchange chromatography. The in vitro system may include detergent or phospholipid to dissolve the hydrophobic substrates and an NADPH generating system, such as provided by glucose 6-phosphate dehydrogenase action on glucose Additionally, as these compounds have diverse biological activity, it is contemplated that selective modulation of the enzymatic activity transforming 7-DHC to 7-DHP and subsequently to hydroxy-7-DHP derivatives and/or vitamin D3-like compounds or, alternatively, transforming vitamin D2 and vitamin D3 to vitDL compounds, can be used for all or some of them to affect the phenotype of cells of ectodermal, endodermal or mesenchymal origin. Also the availability of vitamin D3 and vitamin D2 in vivo may be modified.

More specifically, action of the compounds may include activation of specific receptors for these compounds or of non-receptor regulatory proteins to regulate or modify cellular phenotype. As it is generally accepted that biological substances produced in the body should have their own receptors or binding sites on regulatory proteins, it is contemplated further that there are natural cellular or extracellular proteins with high affinity for specific of these compounds. Binding of these specific compounds to such proteins would modify the metabolic phenotype or metabolic status of the cell or organ targeted.

Thus, these compounds may be efficacious as therapeutics or adjuvant therapeutics for various diseases or simply for cosmetic purposes. In addition, these compounds could act as modifiers of action of other biologically active substances. Overall their action would improve the health status either directly or indirectly by modifying the activity of other biologically active agents.

The following examples are given for the purpose of illustrating various embodiments of the invention and are not meant to limit the present invention in any fashion.

EXAMPLE 1

Biological Materials

Tissue

Human skin and placenta were obtained from discarded biopsy material or surgical specimens, or after delivery. The corresponding protocols were reviewed and approved by the University of Tennessee Institutional Review Board as an exempt protocol under 45 CFR §46.102(F) entitled Skin as neuroendocrine organ with original IBR date of approval of 19 Jul. 2000. RNA from the skin and internal organs of C57BL/6 mice (at telogen and anagen stages of the hair cycle), was isolated as described (33). Mitochondria from Wistar male rat adrenals were obtained using protocols previously described (34). The animal use was approved by appropriate Institutional Animal Care and Use Committees.

Cell Lines

Cultures of normal and immortalized keratinocytes, dermal fibroblasts, melanocytes and melanoma cells were carried out according to standard protocols described previously (12,35-36). Normal human epidermal keratinocytes and melanocytes, and dermal fibroblasts were obtained from Cascade Biologics, Inc. (Portland, Oreg., USA) and cultured as described previously (37).

Mitochondrial Fractions and Enzymes

Mitochondrial fractions of the test tissue, i.e., skin, adrenals or placenta, were prepared by homogenizing the tissue in 5 vols ice-cold 0.25 M sucrose containing protease inhibitor cocktail (Sigma) (38). The homogenate was centrifuged at 600 g for 10 min at 4° C., and the resulting supernatant was centrifuged at 6000 g (placenta) or 9000 g (skin and adrenals) for 20 min at 4° C. to sediment the mitochondrial fraction. The pellet was resuspended in 0.25 M sucrose, and the mitochondrial fraction was again sedimented under the same conditions. The washed mitochondrial fraction was resuspended in 0.25 M sucrose and used for enzymatic reaction. For cultured skin cells, the above procedure was carried out after the cells had been swelled for 30 min in 20 mM HEPES, pH 7.4, before homogenization.

Bovine cytochrome P450scc, adrenodoxin and adrenodoxin reductase were isolated from adrenals (39-40). Human cytochrome P450scc and adrenodoxin were expressed in *Escherichia coli* and purified as describe before (41).

EXAMPLE 2

Synthesis of 7-DHP

The 7-DHP standard was synthesized from pregnenolone acetate following protocols described in (27). The chemical structure of the standard had been confirmed by NMR analysis. The standard was further purified by RP-HPLC and stored at −70° C.

EXAMPLE 3

Enzymatic Assays

Side-chain Cleavage of 7-DHC

Large-scale reactions (50 mL) to cleave the side chain of 7-DHC were performed with purified bovine P450scc and its electron-transfer system in a manner similar to that described for cholesterol (41). The incubation mixture comprised 510 µM phospholipids vesicles (dioleoylphosphatidylcholine plus 15 mol % cardiolipin) with a substrate to phospholipids molar ration of 0.2 50 µM NADPH, 2 mM glucose 6-phosphate, 2 U-mL$^{-1}$ glucose 6-phosphate dehydrogenase, 0.3 µM adrenodoxin reductase, 6.5 µM adrenodoxin, 1.0 µM cytochrome P450scc and buffer, pH 7.4 (41). After incubation at 37° C. for 3 h, the mixture was extracted three times with 50 mL methylene chloride and dried under nitrogen at 35° C. Products were purified by preparative TLC on silica gel G with three developments in hexane/ethyl acetate (3:1 v/v) and products eluted from the silica gel with chloroform/methanol (1:1, v/v). Samples were dried under nitrogen and shipped for analysis on dry ice. Small-scale reactions (0.25 mL) to determine the kinetics of 7-DHC and cholesterol metabolism were performed with either bovine or human cytochrome P450scc as described for cholesterol (41). The amount of 7-DHP produced from 7-DHC was measured by RIA [25] using purified 7-DHP as standard.

Side-chain Cleavage by Mitochondria Isolated from Skin Cells

[4-$^{14}$C]Cholesterol (58 mCi.mmol$^{-1}$; Amersham Bioscience) was purified before its use as a substrate by mitochondria, by TLC on silica gel G plates in hexane/acetone (7:3, v/v). Isolated mitochondria (0.5 mg protein) were then preincubated (15 min at 37° C.) with purified [4-$^{14}$C] cholesterol (1 µCi, 34 µM) in 0.5 mL medium comprising 0.25M sucrose, 50 mM HEPES, pH 7.4, 20 mM KCl, 5 mM MgSO$_4$, 0.2 mM EDTA, 0.4 µM adrenodoxin reductase, 6 µM adrenodoxin, 5 µM N-62 StAR protein (gift from W. Miller, University of California, San Francisco, Calif., USA) and 8 µM cyanoketone. The reaction was started by adding NADPH (0.5 mM) and isocitrate (5 mM), and samples were incubated at 37° C. for 150 min. The reaction was stopped by the addition of 1 mL ice-cold methylene chloride, and the incubation mixture extracted twice more with 1 mL methylene chloride. The fractions were combined, dried under nitrogen, and subjected to TLC on silica gel G plates and developed with hexane/acetone (7:3, v/v). Radiolabelled products were visualized using a phosphoimager, the steroids eluted from the plate with chloroform/methanol (1:1, v/v), and the associated radioactivity measured by scintillation counting.

Side-chain Cleavage of 7-DHC by Placental and Adrenal Mitochondria

Incubations were carried out as described for skin mitochondria except that radiolabelled cholesterol was replaced with 200 μM 7-DHC, exogenous adrenodoxin and adreno- FDXR cDNAs were routinely amplified by a single PCR (30 cycles), and in selected experiments human CYP11A1, a transcript of 628 bp, was also amplified by nested PCR. The sequence and exonal localization of the primers in the corresponding genes are presented in Table 1.

TABLE 1

Primer Sequences

| Gene | Primer | Primer Sequences | Primer Location | Amplified band, (bp) |
|---|---|---|---|---|
| Human genes | | | | |
| FDX1 | P553 | GTGATTCTCTGCTAGATGTTG (SEQ ID NO: 1) | exon 2 | 257 |
|  | P554 | GGCACTCGAACAGTCATATTG (SEQ ID NO: 2) | exon 4 | |
| FDXR | P557 | ATTAAGGAGCTTCGGGAGATG (SEQ ID NO: 3) | exon 7 | 380 |
|  | P558 | CTCTTATACCCAATGCTGCTG (SEQ ID NO: 4) | exon 10 | |
| CYP11A | First pair | | | |
|  | P561 | GCCTTTGAGTCCATCACTAAC (SEQ ID NO: 5) | exon 4 | 628 |
|  | P562 | CCAGTGTCTTGGCAGGAATC (SEQ ID NO: 6) | exon 8 | |
|  | Nested pair | | | |
|  | P563 | ATGTGGCTGCATGGGACGTG (SEQ ID NO: 7) | exon 4 | 390 |
|  | P564 | TCTGCAGGGTCACGGAGATG (SEQ ID NO: 8) | exon 7 | |
| Mouse genes | | | | |
| FDX1 | P581 | AAATTGGCGACTCTCTGCTAG (SEQ ID NO: 9) | exon 2 | 295 |
|  | P582 | CTTGCTCATGTCAACAGACTG (SEQ ID NO: 10) | exon 4 | |
| FDXR | P583 | CTTGGAGTCATCCCCAACAC (SEQ ID NO: 11) | exon 10 | 281 |
|  | P584 | TGGCCTCGAGAGACTTCCTC (SEQ ID NO: 12) | exon 12 | |
| CYP11A | P585 | AGACTTCTTTCGACTCCTCAG (SEQ ID NO: 13) | exon 4 | 693 |
|  | P586 | CTGAAGTTCTCCAGCAGATTG (SEQ ID NO: 14) | exon 8 | | doxin reductase were not added, and the incubation volume was 1.0 mL (placental) or 0.5 mL (adrenal). Extracted products from placenta incubation were analyzed by TLC on silica gel G plates developed three times with hexane/ethyl acetate (3:1, v/v) and visualized by charring; products from adrenal incubations were dissolved in methanol and subjects to LC/MS analysis.

EXAMPLE 4

RT-PCR Amplifications

Tissues and cells were homogenized in Trizol (Invitrogen), and the isolation of RNA followed the manufacture's protocol. The synthesis of first-strand cDNA was performed using the Superscript preamplification system (Invitrogen). Either 5 μg of total of 0.05 μg of poly(A) mRNA per reaction was reverse-transcribed according to the manufacturer's protocol using oligo(dT) as the primer.

All samples were standardized for the analysis by amplification of the housekeeping gene GAPDH as described previously (42). Human and mouse CYP11A1, FDX1 and The reaction mixture (25 μL) contained 2.5 mM g $Cl_2$, 0.25 mM each dNTP, 0.4 μM each primer, 75 mM Tris/HCl (pH 8.8), 20 mM $(NH_4)_2SO_4$, 0.01% (v/v) Tween 20 and 1.25 U Taq polymerase (Promega). The mixture was heated to 94° C. for 2.5 min, and then amplified for 30 cycles as specified: 94° C. for 30 s (denaturation), 55° C. for 20 s (annealing), and 72° C. for 40 s (extension). For nested PCR an aliquot was transferred to a new tube for amplification with the nested pair of primers.

Amplification products were separated by agarose electrophoresis and visualized by ethidium bromide staining (42). The identified PCR products were excised from the agarose gel and purified using a GFX PCR DNA and gel band purification kit (Amersham-Pharmacia-Biotech). PCR fragments were cloned in pGEM-T easy vector system (Promega) and purified with a plasmid purification kit (Qiagen). Sequencing was performed at the Molecular Resource Center at the University of Tennessee HSC (Memphis, Tenn., USA) using Applied Biosystems 3100 Genetic Analyzer and BigDye™ Terminator Kit.

EXAMPLE 5

Western Blotting

The methodology followed standard protocols (34,43). Briefly, mitochondrial fractions prepared as described above for detection of P450scc or adrenodoxin reductase or proteins extracted with 1% (v/v) Triton X-100 (to test StAR expression) from placenta, skin or cultured cells were dissolved in Laemmli buffer and separated on an SDS/12% polyacrylamide gel, transferred to am Immobilon P (poly (vinyliden difloride) membrane (Millipore Corp., Bedford, Mass., USA); nonspecific binding sites were blocked by incubation in 5% (v/v) nonfat powdered milk in buffer containing 50 mM Tris/HCl, pH 7.5, 150 mM NaCl, and 0.01% (v/v) Tween-20, for 3 h at room temperature. Membranes were incubated overnight at 4° C. with polyclonal antisera raised in rabbits as follows: anti(bovine P450scc) diluted 1:1000, anti-(porcine adrenodoxin reductase) diluted 1:1000, or anti-StAR protein diluted 1:2000 (44). In parallel incubations, nonimmune serum was used as the control. Next day, membranes were washed and incubated for 1 h with goat anti-rabbit IgG coupled to horseradish peroxidase, diluted 1:10000 (Santa Cruz Biotechnology). Membranes were washed, and bands were visualized with ECL reagent (Amersham Pharmacia Biotech) according to the manufacturer's instructions. For the blots with anti-StAR serum, the secondary antibody was coupled to alkaline phosphatase (1:2000 dilution) and color developed as before (44).

EXAMPLE 6

Analytical Methods

NMR

Samples were dissolved in $CDCl_3$ (Cambridge Isotope Laboratories, Inc., Andover, Mass., USA) and referenced to the residual solvent signal (δ 7.24 p.p.m.). Proton and proton-detected 2D spectra (gradient-enhanced correlation spectroscopy, gradient heteronuclear multiple quantum coherence and gradient heteronuclear multiple bond correlation) were recorded on a Bruker DRX 500-MHz NMR spectrometer equipped with a Nalorac3 mm inverse Z-axis gradient probe (MIDG-500). Carbon and distortionless enhancement by polarization transfer spectra were recorded on a Varian Unit Inova 600-MHz spectrometer equipped with a Nalorac 3 mm direct detect probe (MDBC600F). The NMR data were processed using XWINNMR 3.7 running on Red Hat Linux 7.3.

LC/MS Analysis

RP-HPLC and MS analysis was performed on a high-performance liquid chromatography mass spectrometer LCMS-QP8000α (Shimadzu, Tokyo, Japan) equipped with a Restec Allure C18 column (150×4.6 mm; 5 µm particle size; 60 Å pore size), UV/VIS photodiode array detector (SPD-M10Avp) and quadropole mass spectrometer. The LC/MS workstation CLASS-8000 software was used for system control and data acquisition (Shimadzu). Elution was carried out isocratically at a flow rate of 0.5 mL·min$^{-1}$ and temperature of 40° C. The mobile phase from 0 to 30 min consisted of 85% (v/v) methanol and 0.1% (v/v) acetic acid, and from 30 to 75 min of 98% (v/v) methanol and 0.1% (v/v) acetic acid. The mass spectrometer was operated in atmospheric pressure chemical ionization; positive ion mode was used with nitrogen as the nebulizing gas. The MS parameters were as follows: nebulizer gas flow rate 2.5 L·min$^{-1}$; probe high voltage 3.5 kV; probe temperature 300° C.; curved desolvation line heater temperature 230° C. Analyses were carried out in the scan mode from m/z 310-415.

EXAMPLE 7

Detection and Expression of P450scc (CYP11A1), Adrenodoxin and Adrenodoxin Reductase Genes in Skin Genes coding for P450scc (CYP11A1) are expressed in mouse and human skin samples that include human biopsy specimens, subcutaneous adipose tissue and epidermal and dermal cell lines, e.g., normal epidermal and immortalized (HaCaT) keratinocytes, dermal fibroblasts, squamous cell carcinoma, five human melanomas at diffeent levels of progression (FIGS. 2A-2F) and the Cloudman S91 mouse melanoma line. Nested RT-PCR revealed general CYP11A1 gene expression that was below the level of detectability only in human epidermal melanocytes and in a single melanoma line (SKMEL-188) (FIG. 2A). The lower band detected in keratinocytes, squamous cell carcinoma and melanoma cells (FIG. 2A, lanes 2-3, 8, 10-11) represents an additional alternatively spliced CYP11A1 isoform of 229 bp (GeneBank No. AY603498). Direct RT-PCR (30 cycles) showed expression of CYP11A1 in anagen and telogen murine skin and the Cloudman S91 mouse melanoma line (FIG. 2D). The genes for adrenodoxin (FDX1) and adrenodoxin reductase (FDXR) were consistently expressed in all samples tested (FIGS. 2B-2C, 2E-2F). In FIG. 1C, in addition to the correct transcript of 380 bp, confirmed by sequencing, there are additional bands that may represent either alternatively spliced variants or nonspecific DNA fragments (not sequenced).

The corresponding mRNAs were further translated into proteins producing immunoreactive species recognized by specific antibodies (FIGS. 3A-3C). These immunoreactive products had molecular masses compatible with those expected for processed P450SCC (50-55 kDa) (FIGS. 3A-3B) and adrenodoxin reductase (48 kD) FIG. 3C). The protein components of P450scc were detected in control placenta, whole human skin, normal epidermal and immortalized keratinocytes, dermal fibroblasts, squamous cell carcinoma and five human melanomas. These data clarify in detail the cutaneous expression of the P450scc system.

EXAMPLE 8

Detection of Cholesterol Transporting Proteins

Using specific antibodies that recognize a common epitope for both MLN64 and StAR (21), the expected protein with molecular mass in the 48-55 kDa range corresponding to MLN64 (24) was detected in placenta, human skin, and human, mouse and hamster melanoma cells (FIGS. 4A-4B). Two major bands in the 48-55 kDa range are present in the placenta, as reported previously (23). The multiple bands are believed to result from proteolytic processing. These bands and other smaller ones aalso are seen when the MLN64 gene is transfected into COS-1 cells (23). The relative proportions of the two bands in the 48-55 kDa range in human skin are similar to that in the human placenta (FIG. 3A, lanes 2-3), but the proportion varies in the different cell types tested, indicating different levels of processing. The additional immunoreactive proteins of lower molecular mass, i.e., 37 kD and 18 kD, present in some melanoma lines represent either further products of MLN64 processing (21,23) and/or the full-length StAR protein (20).

EXAMPLE 9

In Vitro Production of Steroids from Cholesterol

Incubation of mitochondria from skin cells, i.e., immortalized and malignant keratinocytes, with [4-$^{14}$C]cholesterol resulted in the production of steroids that migrated at the same rate as pregnenolone and progesterone standards (FIG. 5). The calculated rates of conversion of [4-$^{14}$C]cholesterol into pregnenolone and progesterone in cutaneous mitochondria were 0.14% and 0.04%, respectively, ~1% of the conversion reported for placental mitochondria (29).

Pregnenolone was also detected by RIA in the culture medium after incubation of these cells for 18 hours with 25 µM 22R-hydroxycholesterol and 8 µM cyanoketone, a 3β-HSD inhibitor. Pregnenolone was not detected after incubation with 22R-hydroxycholesterol alone suggesting its rapid metabolism, most likely via the delta-4 pathway. A similar observation was made in the WM164 melanoma line. Thus, not only do whole skin and a wide spectrum of skin cells express the gene and proteins necessary for the activity of the P450scc system in vivo, but a wide spectrum of skin cells also share the same properties, but this cutaneous P450scc system is functional as it does exhibit cholesterol side chain shortening activity leading to actual production of pregnenolone.

EXAMPLE 10

7-DHC is a Substrate for P450scc

Since 7-dehydrocholesterol accumulates in the skin, this sterol was tested as an alternate substrate for cytochrome P450scc. This required the chemical synthesis of a 7-dehydropregnenolone standard whose identity was confirmed by NMR analysis (not shown). Purified P450scc enzyme supplemented with adrenodoxin and adrenodoxin reductase did indeed transform 7-dehydrocholesterol to a product identical to the 7-dehydropregnenolone standard as determined by identical migration rate on TLC, retention time on RP-HPLC and UV absorption spectrum (not shown).

A UV spectrum of this biotransformation product showed a very characteristic pattern of bands at 272, 282, and 294 nm with a shoulder at 263 nm. These UV data are in full agreement with published data for 7-dehydropregnenolone (25-27). GC/MS analysis of this product shows a mass spectra pattern identical to that reported most recently by Guryev (19) confirming authenticity of 7-dehydropregnenolone.

Definitive proof of chemical structure was obtained with NMR that showed all resonance signals characteristic of 7-dehydropregnenolone (FIG. 6A). The $^1$HNMR spectrum of the biotransformation product is in agreement with that of the chemically synthesized standard (FIG. 6B) and with the data from literature data (26). Thus, two angular methyl groups, 18- and 19-CH$_3$, showed resonance signals at 0.56 and 0.90 ppm, respectively. The methyl group in the side chain, 21-CH$_3$, gave the singlet at 2.12 ppm due to the presence of an adjacent keto group at C-20. The signal of the methane proton (3αH) at the secondary alcohol was shown as a multiplet at 3.61 ppm. Finally, two very characteristic signals for steroidal 5,7-diene system, 6- and 7-H, appeared as AB quartet at 5.40 and 5.52 ppm with the coupling constants $J_1$=6 Hz and $J_2$=0.5 Hz. Lastly, $^{13}$CNMR and 2D-NMR data, i.e., COSY, HMQC, and HMBC, fully and unequivocally confirmed the structure of the product generated by the reaction of 7-dehydrocholesterol with P450scc as 7-dehydropregnenolone.

EXAMPLE 11

Reaction Kinetics

Reaction kinetics for 7-dehydrocholesterol conversion to 7-dehydropregnenolone by bovine P450scc, as determined with the substrate dissolved in the membrane of phospholipid vesicles, were similar to those for the conversion of cholesterol to pregnenolone, with the catalytic rate constant ($k_{cat}$) for 7-DHC being 62% of that for cholesterol. Human P450scc had a $k_{cat}$ value for 7-DHC 70% of that for cholesterol and a lower $K_m$. This gives human P450scc a slightly higher $k_{cat}/K_m$ value with 7-dehydrocholesterol as substrate than with cholesterol. In comparison, Guryev et al. (19) recently reported that bovine P450scc had the same $V_{max}$ for 7-DHC and cholesterol in an assay of P450scc where cholesterol was held in solution with 2-hydroxypropyl-β-cyclodextrin. It must be noted that in a reconstituted in vitro system both MLN64 and StAR can interact with 7-DHC and transport it from donor to acceptor vesicles with efficiency similar to that for cholesterol (28).

Table 2 contains the kinetic parameters for side-cahin cleavage of 7-DHC and cholesterol by bovine and human cytochromes P450scc. Kinetic parameters were determined with substrates and P450scc incorporated into dioleoylphosphatidylcholine (PL) vesicles containing cardiolipin. Values for $K_{cat}$ and $K_m$ are ±SE and are expressed as min$^{-1}$ and mol sterol-mol PL$^{-1}$, respectively. They were obtained from fitting hyperbolic curves to the kinetic data using KALEIDAGRAPH.

TABLE 2

| Substrate | Km | kcat | kcat/Km |
|---|---|---|---|
| Human P450scc | | | |
| Cholesterol | 0.164 ± 0.009 | 19.0 ± 0.4 | 116 |
| 7-DHC | 0.103 ± 0.006 | 13.3 ± 0.4 | 129 |
| Bovine P450scc | | | |
| Cholesterol | 0.078 ± 0.011 | 39.3 ± 1.7 | 504 |
| 7-DHC | 0.069 ± 0.010 | 24.4 ± 1.1 | 353 |

Kinetic Parameters

EXAMPLE 12

P450/7-DHC Pathway

The P450/7-DHC pathway must be operative in living cells as mitochondria purified from human placenta (FIG. 7) and rat adrenal (FIGS. 8A-8F) do transform 7-dehydrocholesterol to a 7-dehydropregnenolone as identified by TLC, LC/MS and LC with UV absorption spectra analysis. Incubation of mitochondria with NADPH and isocitrate (FIGS. 8C and 8F) yielded two peaks of ion [M+H] with m/z 315.3 at retention time 8.1 and 15.6 min. The first peak had m/z, retention time and UV spectra (FIG. 8D inset 3) corresponding to the 7-DHP standard (FIGS. 8D inset 2 and 8C inset). The product was the limits of detectability in the control sample with the reaction stopped at time 0 (A) and in mitochondria incubated in the absence of NADPH and isocitrate (FIGS. 8B and 8E). The second peak (unknown) had a retention of 15.6 min and UW spectra (FIG. 8D inset 4) similar to those of the first product and probably represents an additional product of 7-DHC transformation (FIG. 8C). Differing from these reaction products were the parameters for the 7-DHC. The retention time for its ion with m/z 385.3 and UFV spectra are shown in FIG. 8B inset and FIG. 8D inset 1.

The use of 7-dehydrocholesterol as substrate for P450scc provides the likely explanation for the humoral accumulation of 7-DHP and its metabolites in Smith-Lemli-Opitz syndrome (17-18), and is indicative of pathway activation in vivo, at least under pathological conditions. Epidermal availability of 7-DHC in conjunction with the presence of an active P450scc system makes it probable that 7-DHP is produced in the skin. In contrast, under physiological conditions the highly specific analytical assays used herein were not sensitive enough to detect production of 7-dehydropregnenolone in unstimulated basal skin. Presumably, this is related to the low conversion rate for cholesterol itself in cutaneous mitochondria, as demonstrated in FIG. 5. Thus, cutaneous mitochondria converted only 0.14% and 0.04% of [4-$^{14}$C]-cholesterol to pregnenolone and progesterone, respectively, which is approximately 1% of the conversion reported for placental mitochondrai (29).

EXAMPLE 13

Vitamin D3 is a Substrate for P450scc

Since 7-dehydrocholesterol is a precursor to vitamin D3, i.e., cholecalciferol or 5Z,7E-9,10-secocholesta-5,7,10(19)-trien-3β-ol, P450scc was tested to determine if the enzyme can shorten the side chain in the vitamin D3 substrate. The incubation of the enzyme with vitamin D3 substrates generated 3 compounds, 1D, 2D and 3D, migrating on the TLC plate at different rates than vitamin D3 precursor and having the UV spectra similar to vitamin D3, indicating presence of double bonds (FIG. 9). Similar observation was reported most recently by Guryev (19).

Compounds 1D and 3D were identified by NMR as 20-hydroxy vitamin D3 and 20,22-dihydroxy vitamin D3, which is in agreement with Guryev et al results (19) indicating step-wise formation of 20,22-dihydroxy vitamin D3 from vitamin D3 by P450scc system. The product 2D migrating between D1 and D3 at TLC and at a similar rate as pregnenolone may represent 5Z,7E-9,10-secopregna-5,7, 10(19)-triene-3β,20α-diol as a result of complete side chain cleavage.

EXAMPLE 14

Vitamin D2 is a Substrate for P450scc

Vitamin D2, i.e., ergocalciferol or 9,10-seco(5Z,7E)-5,7, 10(19),21-ergostatetrane-3β-ol, can be transformed by cytochrome P450scc system to at least two products P1 and P3 that are different from pregnenolone P2 (FIG. 10). By analogy with vitamin D3 it is contemplated that product P1 is 20-hydroxy vitamin D2, while P3 is a dihydroxy vitamin D2 with one hydroxyl-group located at position C20. Positioning of the second hydroxyl is most likely precluded at positions C22 or C23 within the C17 side chain because presence of double bond therebetween prevents hydroxylation at these positions. Additionally, hydroxylation does not occur at positions C24 or C25 within the C17 side chain because the chemical shift and multiplicity of all methyl groups except C21 methyl do not change very much. Without being held to theory, is contemplated that the second hydroxy may be positioned at C14.

The vitamin D2 precursor erogosterol can be transformed by the cytochrome P450scc system to two products identified as 20-hydroxyergosterol and dihydroxyergosterol by analogy with the process above (FIGS. 11A-11C). As with the dihydroxy vitamin D2, dihydroxyergosterol will have one hydroxy group located at position C20. Again as with dihydroxy vitamin D2 it is contemplated that the second hydroxy may be positioned at C14.

The following references are cited herein.
1. Slominski, A. and Wortsman, J. *Endocr Rev* 21, 457 (2000).
2. Slominski, et al. *Physiol Rev* 80, 979 (2000).
3. A. Slominski et al., *Faseb J* 15, 1678 (2001).
4. Holick, M F, *J Cell Biochem* 88, 296 (2003).
5. Kamradt et al., *Recent Results Cancer Res* 164, 259 (2003).
6. Holick, M F, *Recent Results Cancer Res* 164, 3 (2003).
7. Tian, X Q and Holick, M F, *J Biol Chem* 274, 4174 (1999).
8. Lambeth, et al. *Mol Cell Biochem* 45, 13 (1982).
9. Tuckey, R C and Sadleir, J, *Eur J Biochem* 263, 319 (1999).
10. Slominski, et al. *J Clin Endocrinol Metab* 81, 2746 (1996).
11. Slominski, et al. *FEBS Lett* 455, 364 (1999).
12. Slominski et al., J Invest Dermatol 118, 310 (2002).
13. Rogoff, et al. *J Steroid Biochem Mol Biol* 78, 77 (2001).
14. Slominski, et al. *Biochim Biophys Acta* 1474, 1 (2000).
15. Nowaczyk, M J and Waye, J S, *Clin Genet* 59, 375 (2001).
16. Tint et al., *N Engl J Med* 330,107 (1994).
17. Shackleton, et al. *Steroids* 64, 481 (1999).
18. Shackleton, et al. J Steroid Biochem Mol Biol 82, 225 (2002).
19. Guryev, et al. *Proc Natl Acad Sci USA* 100, 14754 (2003).
20. Stocco, D M, *Biochim Biophys Acta* 1486, 184 (2000).
21. Bose, et al. *Biochemistry* 39, 11722 (2000).
22. Thiboutot et al., *J Invest Dermatol* 120, 905 (2003).
23. Watari et al., *Proc Natl Acad Sci USA* 94, 8462 (1997).
24. Uribe, et al. *Arch Biochem Biophys* 413, 172 (2003).
25. Tait, et al. *J Endocrinol* 99, 87 (1983).
26. Murari, et al. *J Steroid Biochem* 17, 615 (1982).
27. Noboru, et al. U.S. Pat. No. 4,891,364 (1990).
28. Tuckey, R C (unpublished data).
29. Boguslawski, W, *J Steroid Biochem* 18, 771 (1983).
30. Irons et al., *Am J Med Genet* 68, 311 (1997).
31. Sanai, et al. *Nippon Sanka Fujinka Gakkai Zasshi* 36, 195 (1984).
32. Pescador, et al. *Biol Reprod* 55, 485 (1996).
33. Slominski et al. J. Invest. Dermatol. 96, 172 (1991).
34. Slominski et al. J. Invest. Eur. J. biochem. 270, 335 (2003).
35. Slominski et al. J. Cell Sci. 89, 287 (1988).
36. Slominski et al. FASEB J. 16, 896 (2002).
37. Slominski et al. Endocrinology 145, 941 (2003).
38. Tuckey, R C and Cameron, K J, Eur. J. Biochem
39. Tuckey, R C and Stevenson, P M, Int. J. Biochem. 16, 489 (1984).
40. Tuckey, R C and Stevenson, P M, Int. J. Biochem. 16, 497 (1984).
41. Woods et al. Arch. Biochem. Biophys. 353, 109 (1998).
42. Piarchik, A and Slominski, A T, FASEB J. 15, 2754 (2001).

43. Slominski et al. Biochim. Biophys. Acta 1639, 80 (2003).
44. Tuckey et al. Mol. Cell. Endocrinol. 105, 103 (1994).
45. Guo et al. Steroids 68, 31-42 (2003).
46. Marcos et al. Steroids 69, 51-60 (2004).

Any publications mentioned in this specification are indicative of the levels of those skilled in the art to which the invention pertains. Further, these publications are incorporated by reference herein to the same extent as if each individual publication was specifically and individually incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A compound that is 5Z,7E-3β,11α-dihydroxy-9,10-secopregna-5,7,10(19)trien-20-one, 5Z,7E-3β,11β-dihydroxy-9,10-secopregna-5,7,10(19)trien-20-one, 5Z,7E-3,17β-dihydroxy-9,10-secopregna-5,7,10(19)trien-20-one, 5Z,7E-3,β,21-dihydroxy-9,10-secopregna-5,7,10(19)trien-20-one, 5Z,7E-3β,17β,21-trihydroxy-9,10-secopregna-5,7,10(19)trien-20-one, 5Z,7E-3β,11α,17β-trihydroxy-9,10-secopregna-5,7,10(19)trien-20-one, 5Z,7E-3β,11β,17β-trihydroxy-9,10-secopregna-5,7,10(19)trien-20-one, 5Z,7E-3β,11α,21-trihydroxy-9,10-secopregna-5,7,10(19)trien-20-one, 5Z,7E-3β,11β,21-trihydroxy-9,10-secopregna-5,7,10(19)trien-20-one, 5Z,7E-3β,11α,17β,21-tetrahydroxy-9,10-secopregna-5,7,10(19)trien-20-one, 5Z,7E-3β,11β,17β,21-tetrahydroxy-9,10-secopregna-5,7,10(19)trien-20-one, 3-keto-17-hydroxyetiocalciferal or 3,17-diketoetiocalciferol.

* * * * *